US010392620B2

(12) United States Patent
Delgado et al.

(10) Patent No.: US 10,392,620 B2
(45) Date of Patent: Aug. 27, 2019

(54) CYTOCHROME B (CYTB) NUCLEIC ACID MOLECULES THAT CONTROL PATHOGENS

(71) Applicant: Dow AgroSciences LLC, Indianapolis, IN (US)

(72) Inventors: Javier A. Delgado, Indianapolis, IN (US); Justin M. Lira, Zionsville, IN (US); Chaoxian Geng, Zionsville, IN (US); Meghan L. Frey, Greenwood, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/800,153

(22) Filed: Nov. 1, 2017

(65) Prior Publication Data

US 2018/0127760 A1 May 10, 2018

Related U.S. Application Data

(60) Provisional application No. 62/419,988, filed on Nov. 10, 2016.

(51) Int. Cl.

| | |
|---|---|
| *C12N 15/82* | (2006.01) |
| *C12N 15/113* | (2010.01) |
| *A01N 57/16* | (2006.01) |

(52) U.S. Cl.
CPC .......... *C12N 15/1138* (2013.01); *A01N 57/16* (2013.01); *C12N 15/8218* (2013.01); *C12N 15/8282* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 8,865,968 B2 * | 10/2014 | Van De Craen | A01N 63/02 536/24.5 |
| 9,121,022 B2 * | 9/2015 | Sammons | A01N 63/02 |
| 2006/0247197 A1 | 11/2006 | Van De Craen | |
| 2010/0257634 A1 | 10/2010 | Bailey | |
| 2010/0311819 A1 | 12/2010 | Van de Craen | |
| 2015/0051231 A1 | 2/2015 | Borges | |
| 2015/0082495 A1 | 3/2015 | Bayer | |

FOREIGN PATENT DOCUMENTS

| | | | | |
|---|---|---|---|---|
| WO | WO2013/050410 A1 | 4/2013 | |
| WO | 2016/109758 A2 | 7/2016 | |
| WO | WO-2017212315 A1 * | 12/2017 | A01H 1/00 |
| WO | WO2017212315 A1 | 12/2017 | |

OTHER PUBLICATIONS

Thomas et al, 2001, Plant J., 25:417-425.*
Fraaije et al, 2005, Ecology and Epidemiology, 95:933-941.*
Allioui et al, 2016, Phytopathologia Mediterranea, 55:89-97.*
Koch, A., et al., 2016. An RNAi-based control of Fusarium graminearum infections through spraying of long dsRNAs involves a plant passage and is controlled by the fungal silencing machinery. PloS Pathogens 12 (10):e1005901.

Mumbanza, F., et al., . 2013. In vitro antifungal activity of synthetic dsRNA molecules against two pathogens of banana, *Fusarium oxysporum* m f.sp. *cubense* and *Mycosphaerella fijiensis*. Pest Management Science 69:1155-1162.

Koch, A. et al., 2013. Host-induced gene silencing of cytochrome P450 lanosterol C14a-demethylase-encoding genes confers strong resistance to *Fusarium* species. PNAS 110(48):19324-19329.

Fraaije, B. A., et al. “Role of ascospores in further spread of Qol-resistant cytochrome b alleles (G143A) in field populations of Mycosphaerella graminicola.” Phytopathology 95.8 (2005): 933-941.

Delgado, J. A., et al. “Identification of the mutation responsible for resistance to Qol fungicides and its detection in Ascochyta rabiei (teleomorph Didymella rabiei).” Plant Pathology 62.3 (2013): 688-697.

International Search Report and Written Opinion for International Application No. PCT/US17/59434, dated Mar. 19, 2018.

Baulcombe. “RNA silencing in plants.” Nature 431.7006 (2004): 356.

Hannon. “RNA interference.” nature 418.6894 (2002): 244.

* cited by examiner

*Primary Examiner* — Jason Deveau Rosen

(57) ABSTRACT

This disclosure concerns nucleic acid molecules and methods of use thereof for control of pathogens through RNA interference-mediated inhibition of target coding and transcribed non-coding sequences in pathogens. The disclosure also concerns methods for applying dsRNA through formulations and/or transgenic plants that express nucleic acid molecules useful for the control of pathogens, and the plant cells and plants obtained thereby.

42 Claims, 1 Drawing Sheet

Specification includes a Sequence Listing.

Generation of dsRNA from two templates with two pairs of primers.
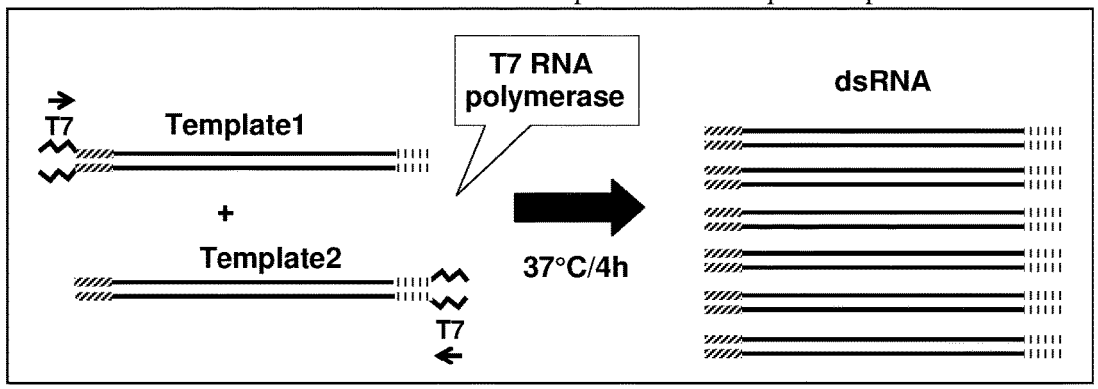

CYTOCHROME B (CYTB) NUCLEIC ACID MOLECULES THAT CONTROL PATHOGENS

CROSS-REFERENCE TO RELATED APPLICATION

This application claims the benefit of the filing of U.S. Provisional Patent Application Ser. No. 62/419,988, filed Nov. 10, 2016, the disclosure of which is hereby incorporated herein in its entirety by this reference.

TECHNICAL FIELD OF THE DISCLOSURE

The present disclosure relates generally to control of plant damage caused by pathogens. In particular embodiments, the present disclosure relates to identification of target coding and non-coding sequences, and the use of recombinant DNA technologies for post-transcriptionally repressing or inhibiting expression of target coding and non-coding sequences in the cells of a pathogen to provide a plant-protective effect.

BACKGROUND

A large amount of crop loss and plant damage is incurred each year due to plant diseases caused by two classes of fungi: Ascomycetes, causing a large number of leaf spots, blights, soil-born and post-harvest diseases; and Basidiomycetes, causing rust, smuts, bunts and soil born-diseases. Also, Oomycetes cause a number of plant diseases including downy mildews, leaf blights and soil-born diseases.

*Zymoseptoria tritici*, also known as *Septoria tritici*, also known as *Mycosphaerella graminicola*, also known as SEPTTR, is an ascomycete in the family Mycosphaerellaceae. This fungus, a species of filamentous fungus, is a wheat plant pathogen that causes *Septoria* leaf blotch. *Septoria* leaf blotch is difficult to control due to the development of resistance to multiple fungicides.

*Zymoseptoria tritici* infects its host through the stomata. There is a long latent period of up to two weeks following infection before symptoms develop (Orton, E. S. et. al., (2011) *Mycosphaerella graminicola*: from genomics to disease control. Molecular Plant Pathology 12(5):413-424). The fungus evades host defenses during the latent phase, followed by a rapid switch to necrotrophy immediately prior to symptom expression 12-20 days after penetration.

Wheat yields can be reduced by 30-50% due to losses caused by *Septoria* leaf blotch (STB) with a huge economic impact (Eyal, Z. et. al., (1987) The *Septoria* Diseases of Wheat: Concepts and Methods of Disease Management. Mexico, DF: CIMMYT). Global costs for fungicides to manage STB total hundreds of millions of dollars each year (Hardwick, N. V. et. al., (2001) Factors affecting diseases of winter wheat in England and Wales, 1989-98. Plant Pathol 50: 453-462; McDougall, P. (2006) Phillips McDougall Agriservice Report. Scotland, UK: Pathhead, Midlothian).

The control of phytopathogenic microorganisms, and in particular, fungi, is of vast economic importance since fungal growth on plants or on parts of plants inhibits production of foliage, fruit or seed, and the overall quality of a cultivated crop. Because of the economic ramifications of fungal propagation in agricultural and horticultural cultivations, a broad spectrum of fungicidal and fungistatic products has been developed for general and specific applications. Fungicides can be separated into two categories according to their fungicidal activity: protectants and curatives. Protectant fungicides, as the name implies, protect the plant against infection. A protectant fungicide must be applied before the pathogen lands on the plant surface and/or the infection process begins. Conversely, a curative fungicide must be able to halt disease development after the infection process has begun. A curative fungicide can be applied after the infection process has begun. Most curative fungicides also have protectant activity.

Inorganic fungicides were generally the first to be used in large-scale crop protection aimed against pathogenic fungi. Notable among these are elemental sulfur applied in powder form, and copper sulfate applied in caustic calcium aqueous mixture. While these inorganic fungicides are generally effective, they have significant drawbacks. The fungicides or derivatives of the fungicides are often environmentally non-recyclable. Additionally, pathogens often develop resistance to synthetic pesticides. Because of the development of resistance, continuous endeavors are needed to develop new crop protecting agents.

A variety of simple structured antimicrobial compounds have been developed. Notable among these are fungicide compositions based on copper, zinc or manganese that have been shown to be effective against a broad range of plant pathogenic fungi and bacteria. Fungicides in this category, unlike the category of inorganic fungicides previously discussed, are generally environmentally friendly and the microbes tend to not develop immunity against them. In certain applications, however, the use of these traditional inorganic fungicides for soil treatment is limited due to the absorption of the metal ions to soil particles.

A need, therefore, remains for antimicrobial compositions that are environmentally safe, cost affordable, and that are highly effective for controlling plant microbes, such as fungi, yeast and bacteria.

RNA interference (RNAi) is a process utilizing endogenous cellular pathways, whereby an interfering RNA (iRNA) molecule (e.g., a dsRNA molecule) that is specific for all, or any portion of adequate size, of a target gene sequence results in the degradation of the mRNA encoded thereby. In recent years, RNAi has been used to perform gene "knockdown" in a number of species and experimental systems; for example, *Caenorhabditis elegans*, plants, fungi, insect embryos, and cells in tissue culture. See, e.g., Fire et al. (1998) Nature 391:806-811; Martinez et al. (2002) Cell 110:563-574; McManus and Sharp (2002) Nature Rev. Genetics 3:737-747; Koch and Kogel (2014) Plant Biotech. J. 12:821-831.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Micro ribonucleic acid (miRNA) molecules may be similarly incorporated into RISC. Post-transcriptional gene silencing occurs when the guide strand binds specifically to a complementary sequence of an mRNA molecule and induces cleavage by Argonaute, the catalytic component of the RISC complex. This process is known to spread systemically throughout some eukaryotic organisms, despite initially limited concentrations of siRNA and/or miRNA, such as plants, nematodes, and some insects.

Only transcripts complementary to the siRNA and/or miRNA are cleaved and degraded, and thus the knock-down of mRNA expression is sequence-specific. In plants, several functional groups of DICER genes exist. The gene silencing effect of RNAi persists for days and, under experimental conditions, can lead to a decline in abundance of the targeted transcript of 90% or more, with consequent reduction in levels of the corresponding protein. In fungi, there are two DICER enzymes, where DICER2 is the major enzyme participating in post-transcriptional gene silencing. On the other hand, DICER1 has a redundant role in the pathway (Catalanotto. C., et al., (2004) Redundancy of the two dicer genes in transgene-induced posttranscriptional gene silencing in *Neurospora crassa*. Molecular Cell Biology 24:2536-2545).

SUMMARY OF THE DISCLOSURE

Disclosed herein are nucleic acid molecules (e.g., target genes, DNAs, dsRNAs, siRNAs, shRNA, miRNAs, and hpRNAs), and methods of use thereof, for the control of pathogens, including, for example, *Zymoseptoria tritici* Desm.; *Zymoseptoria citri*; *Zymoseptoria caryae*; *Zymoseptoria curcurbitacearum*; *Zymoseptoria dianthi*; *Zymoseptoria glycines*; *Zymoseptoria helianthi*; *Zymoseptoria ostryae*; *Puccinia triticina*; *Puccinia striiformis* f. sp. *tritici*; *Phaeosphaeria nodorum*; *Rhyncosporium commune*; *Alternaria solani*; *Cercospora beticola*; *Magnaporthe grisea*; *Venturia inaequalis*; and *Phakopsora pachyrhizi*. In particular examples, exemplary nucleic acid molecules are disclosed that may be homologous to at least a portion of one or more native nucleic acid sequences in *Zymoseptoria*.

In these and further examples, the native nucleic acid sequence may be a target gene, the product of which may be, for example and without limitation: involved in a metabolic process, detoxification process, or structural development. In some examples, post-translational inhibition of the expression of a target gene by a nucleic acid molecule comprising a sequence homologous thereto may be lethal in the pathogen, or result in reduced growth and/or development. In specific examples of cytochrome b, a gene belonging to the mitochondrial respiratory chain complex genes involved in respiratory electron transport (referred to herein as CytB) may be selected as a target gene for post-transcriptional silencing. In particular examples, a target gene useful for post-transcriptional inhibition is the novel gene referred to herein as CytB. An isolated nucleic acid molecule comprising a nucleotide sequence of CytB (SEQ ID NO:1 and SEQ ID NO:3); the complement of CytB (SEQ ID NO:1 and SEQ ID NO:3); and fragments of any of the foregoing is therefore disclosed herein. An isolated nucleic acid of the present disclosure may be operably linked operably to a heterologous promoter.

Also disclosed are nucleic acid molecules comprising a nucleotide sequence that encodes a polypeptide that is at least 85% identical to an amino acid sequence within a target gene product (for example, the product of a gene referred to as CYTB). For example, a nucleic acid molecule may comprise a nucleotide sequence encoding a polypeptide that is at least 85% identical to an amino acid sequence of SEQ ID NO:2 (CYTB protein). In particular examples, a nucleic acid molecule comprises a nucleotide sequence encoding a polypeptide that is at least 85% identical to an amino acid sequence within a product of CYTB. In some embodiments, the nucleic acid molecule is a double-stranded nucleic acid. Further disclosed are nucleic acid molecules comprising a nucleotide sequence that is the reverse complement of a nucleotide sequence that encodes a polypeptide at least 85% identical to an amino acid sequence within a target gene product.

Also disclosed are cDNA sequences that may be used for the production of iRNA (e.g., dsRNA, siRNA, shRNA, miRNA, and hpRNA) molecules that are complementary to all or part of a pathogen target gene, for example: CytB. In particular examples, cDNA molecules are disclosed that may be used to produce iRNA molecules that are complementary to all or part of CytB (e.g., SEQ ID NO:1 and SEQ ID NO:3).

Further disclosed are means for inhibiting expression of an essential gene in a pathogen, and means for protecting a plant from pathogens. A means for inhibiting expression of an essential gene in a pathogen is a single- or double-stranded RNA molecule consisting of at least one of SEQ ID NO:4 (*Zymoseptoria* CytB region 1, herein sometimes referred to as CytBT1), SEQ ID NO:5 (*Zymoseptoria* CytB region 2, herein sometimes referred to as CytBT2), SEQ ID NO:6 (*Zymoseptoria* CytB region 9, herein sometimes referred to as CytBT3), SEQ ID NO:7 (*Zymoseptoria* CytB region T4, herein sometimes referred to as CytBT4), SEQ ID NO:8 (*Zymoseptoria* CytB region T5, herein sometimes referred to as CytBT5), SEQ ID NO:9 (*Zymoseptoria* CytB region T6, herein sometimes referred to as CytBT6), SEQ ID NO:10 (*Zymoseptoria* CytB region T7, herein sometimes referred to as CytBT7), or the complement thereof. Functional equivalents of means for inhibiting expression of an essential gene in a pathogen include single- or double-stranded RNA molecules that are substantially homologous to all or part of a *Zymoseptoria* gene comprising SEQ ID NO:1 or SEQ ID NO:3.

Disclosed are methods for controlling phytopathogens, comprising contacting a phytopathogen with an iRNA (e.g., dsRNA, siRNA, shRNA, miRNA, and hpRNA) molecule that functions upon being taken up by (e.g., ingested, absorbed, translocated within, or taken up by) the pathogen to inhibit a biological function within the pathogen, wherein the iRNA molecule comprises all or part of a nucleotide sequence selected from the group consisting of: SEQ ID NO:1 and SEQ ID NOs:3-10; the complement of SEQ ID NO:1 and SEQ ID NOs:3-10; a native coding sequence of a *Zymoseptoria* organism comprising all or part of any of SEQ ID NO:1 and SEQ ID NOs:3-10; the complement of a native coding sequence of a *Zymoseptoria* organism comprising all or part of any of SEQ ID NO:1 and SEQ ID NOs:3-10; a native non-coding sequence of a *Zymoseptoria* organism that is transcribed into a native RNA molecule comprising all or part of any of SEQ ID NO:1 and SEQ ID NOs:3-10; and the complement of a native non-coding sequence of a *Zymoseptoria* organism that is transcribed into a native RNA molecule comprising all or part of any of SEQ ID NO:1 and SEQ ID NOs:3-10.

In these and further examples, the dsRNAs, siRNAs, shRNAs, miRNAs, and/or hpRNAs may be uptaken and/or contacted by the pathogen. Uptake and/or contact of dsRNAs, siRNA, shRNAs, miRNAs, and/or hpRNAs of the disclosure may then result in RNAi in the pathogen, which in turn may result in silencing of a gene essential for viability of the pathogen and leading ultimately to mortality. Thus, methods are disclosed wherein nucleic acid molecules comprising exemplary nucleic acid sequence(s) useful for control of phytopathogens are provided to a fungal plant pathogen. In particular examples, the pathogen controlled by use of nucleic acid molecules of the disclosure may be *Zymoseptoria*. The foregoing and other features are exemplified in the following Detailed Description of several embodiments, which proceeds with reference to the accompanying FIG. 1.

BRIEF DESCRIPTION OF THE FIGURES

FIG. 1. Generation of dsRNA from two transcription templates.

SEQUENCE LISTING

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand and reverse complementary strand are understood as included by any reference to the displayed strand. In the accompanying sequence listing:

SEQ ID NO:1 shows a DNA sequence comprising CytB from *Zymoseptoria tritici*.

SEQ ID NO:2 shows an amino acid sequence of a CYTB protein from *Zymoseptoria tritici*.

SEQ ID NO:3 shows a DNA sequence comprising CytB mRNA from *Zymoseptoria tritici*.

SEQ ID NO:4 shows a DNA sequence of CytBT1 (region 1) from *Zymoseptoria tritici* that was used for in vitro dsRNA.

SEQ ID NO:5 shows a DNA sequence of CytBT2 (region 2) from *Zymoseptoria tritici* that was used for in vitro dsRNA synthesis.

SEQ ID NO:6 shows a DNA sequence of CytBT3 (region 3) from *Zymoseptoria tritici* that was used for in vitro dsRNA synthesis.

SEQ ID NO:7 shows a DNA sequence of CytBT4 (region T4) from *Zymoseptoria tritici* that was used for in vitro dsRNA synthesis.

SEQ ID NO:8 shows a DNA sequence of CytBT5 (region T5) from *Zymoseptoria tritici* that was used for in vitro dsRNA synthesis.

SEQ ID NO:9 shows a DNA sequence of CytBT6 (region T6) from *Zymoseptoria tritici* that was used for in vitro dsRNA synthesis.

SEQ ID NO:10 shows a DNA sequence of CytBT7 (region T7) from *Zymoseptoria tritici* that was used for in vitro dsRNA synthesis.

SEQ ID NOs:11 to 16 show primers used to amplify portions of a CytB subunit sequence from *Zymoseptoria tritici* comprising CytBT1, CytBT2, and CytBT3.

SEQ ID NO:17 shows a DNA sequence comprising CytB from *Puccinia triticina*.

SEQ ID NO:18 shows a DNA sequence comprising CytB from *Cercospora beticola*.

SEQ ID NO:19 shows a DNA sequence comprising CytB from *Magnaporthe grisea*.

SEQ ID NO:20 shows a DNA sequence comprising CytB from *Phaeosphaeria nodorum*.

SEQ ID NO:21 shows a DNA sequence comprising CytB from *Rhynchosporium secalis*.

SEQ ID NO:22 shows a DNA sequence comprising CytB from *Phakopsora pachyrhizi*.

SEQ ID NO:23 shows a DNA sequence comprising CytB from *Venturia inaequalis*.

SEQ ID NO:24 shows a DNA sequence comprising CytB from *Alternaria solani*.

SEQ ID NO:25 shows a DNA sequence comprising CytB from *Puccinia striiformis*.

SEQ ID NO:26 shows a DNA sequence comprising CytB from *Zymoseptoria tritici* strain AUT1.

SEQ ID NO:27 shows a DNA sequence comprising CytB from *Zymoseptoria tritici* strain DEU2.

SEQ ID NO:28 shows a DNA sequence comprising CytB from *Zymoseptoria tritici* strain FRA3.

SEQ ID NO:29 shows a DNA sequence comprising CytB from *Zymoseptoria tritici* strain FRA6.

SEQ ID NO:30 shows a DNA sequence comprising CytB from *Zymoseptoria tritici* strain GBR22.

SEQ ID NO:31 shows a DNA sequence comprising CytB from *Zymoseptoria tritici* strain LARS15.

SEQ ID NO:32 shows a DNA sequence comprising CytB from *Zymoseptoria tritici* strain NZL12.

SEQ ID NO:33 shows a DNA sequence comprising CytB from *Zymoseptoria tritici* strain OC102.

SEQ ID NO:34 shows a DNA sequence comprising CytB from *Zymoseptoria tritici* strain OC201.

SEQ ID NO:35 shows a DNA sequence comprising CytB from *Zymoseptoria tritici* strain R2004.

SEQ ID NO:36 shows a DNA sequence comprising CytB from *Zymoseptoria tritici* strain UK1.

SEQ ID NO:37 shows a DNA sequence comprising CytB from *Zymoseptoria tritici* strain UK2.

SEQ ID NO:38 shows a DNA sequence comprising CytB from *Zymoseptoria tritici* strain UK3.

SEQ ID NO:39 shows a DNA sequence comprising CytB from *Zymoseptoria tritici* strain UK4.

SEQ ID NO:40 shows a DNA sequence comprising CytB from *Zymoseptoria tritici* strain UK5.

SEQ ID NO:41 shows a DNA sequence comprising CytB from *Zymoseptoria tritici* strain UK6.

SEQ ID NO:42 shows a DNA sequence comprising CytB from *Zymoseptoria tritici* strain UK7.

SEQ ID NO:43 shows a DNA sequence comprising CytB from *Zymoseptoria tritici* strain US184.

SEQ ID NO:44 shows a DNA sequence of a T7 phage promoter.

SEQ ID NO:45 shows a DNA sequence of a YFP coding region.

DETAILED DESCRIPTION

I. Overview of Several Embodiments

Disclosed herein are methods and compositions for control of fungal plant pathogen. Methods for improving the yield of a crop are also provided. In addition, methods for identifying one or more gene(s) essential to the lifecycle of a pathogen for use as a target gene for RNAi-mediated control of a pathogen population are provided. In some embodiments, methods are provided for post-transcriptional repression of expression or inhibition of a target gene via nucleic acid molecules that are complementary to a coding or non-coding sequence of the target gene in a pathogen. In these and further embodiments, a pathogen may uptake one or more dsRNA, siRNA, shRNA, miRNA, and/or hpRNA molecules transcribed from all or a portion of a nucleic acid molecule that is complementary to a coding or non-coding sequence of a target gene, thereby providing a plant-protective effect.

Thus, some embodiments involve sequence-specific inhibition of expression of target gene products, using dsRNA, siRNA, shRNA, miRNA, and/or hpRNA that is complementary to coding and/or non-coding sequences of the target gene(s) to achieve at least partial control of a pathogen. Disclosed is a set of isolated and purified nucleic acid molecules comprising a nucleotide sequence, for example, as set forth in any of SEQ ID NO:1, SEQ ID NOs:3-10, SEQ ID NOs: 17-43, and fragments thereof. In some embodiments, a stabilized dsRNA molecule may be expressed from this sequence, fragments thereof, or a gene comprising one of these sequences, for the post-transcriptional silencing or inhibition of a target gene. In certain embodiments, isolated and purified nucleic acid molecules comprise all or part of SEQ ID NO:1. In other embodiments, isolated and purified nucleic acid molecules comprise all or part of SEQ ID NO:3. In still further embodiments, isolated and purified nucleic acid molecules comprise all or part of SEQ ID NO:4. In other embodiments, isolated and purified nucleic acid molecules comprise all or part of SEQ ID NO:5. In other embodiments, isolated and purified nucleic acid molecules comprise all or part of SEQ ID NO:6. In yet other embodiments, isolated and purified nucleic acid molecules comprise all or part of SEQ ID NO:7, SEQ ID NO:8, SEQ ID NO:9, or SEQ ID NO:10.

Particular embodiments involve a recombinant host cell having in its genome a recombinant DNA sequence encoding at least one iRNA (e.g., dsRNA) molecule(s) comprising all of SEQ ID NO:1 and/or SEQ ID NO:3, or a fragment thereof (e.g., SEQ ID NOs: 4-10). When contacted by a pathogen, the iRNA molecule(s) may silence or inhibit the expression of a target gene comprising SEQ ID NO:1, SEQ ID NO:3, or a fragment thereof (e.g., SEQ ID NOs: 4-10) in the pathogen, and thereby result in cessation of growth, development, reproduction, and/or feeding in the pathogen.

Also disclosed herein are methods for delivery of control agents, such as an iRNA molecule, to a pathogen. Such control agents may cause, directly or indirectly, an impairment in the ability of the pathogen to feed, grow, or otherwise cause damage in a host. In some embodiments, a method is provided comprising delivery of a stabilized dsRNA molecule to a pathogen to suppress at least one target gene in the pathogen, thereby reducing or eliminating plant damage by a pathogen. In some embodiments, a method of inhibiting expression of a target gene in a pathogen may result in the cessation of growth, development, reproduction, and/or feeding in the pathogen. In some embodiments, the method may eventually result in death of the pathogen.

In some embodiments, compositions (e.g., a topical composition) are provided that comprise an iRNA (e.g., dsRNA) molecule of the disclosure for use in plants, animals, and/or the environment of a plant or animal to achieve the elimination or reduction of a pathogen infection. In particular embodiments, the composition may be a nutritional composition or food source to be uptaken by the pathogen. Some embodiments comprise making the nutritional composition or food source available to the pathogen. Uptake of a composition comprising iRNA molecules may result in the uptake of the molecules by one or more cells of the pathogen, which may in turn result in the inhibition of expression of at least one target gene in cell(s) of the pathogen. Uptake of or damage to a plant or plant cell by a pathogen may be limited or eliminated in or on any host tissue or environment in which the pathogen is present by providing one or more compositions comprising an iRNA molecule of the disclosure in the host of the pathogen.

In other embodiments, the composition may be a topical composition. Some embodiments comprise making the topical composition available to the pathogen. Contact of a composition comprising iRNA molecules may result in the uptake of the molecules by one or more cells of the pathogen, which may in turn result in the inhibition of expression of at least one target gene in cell(s) of the pathogen. Damage to a plant or plant cell by a pathogen may be limited or eliminated in or on any host tissue or environment in which the pathogen is present by providing one or more compositions comprising an iRNA molecule of the disclosure in the host of the pathogen.

II. Abbreviations dsRNA double-stranded ribonucleic acid
NCBI National Center for Biotechnology Information
gDNA genomic deoxyribonucleic acid
iRNA inhibitory ribonucleic acid
ORF open reading frame
RNAi ribonucleic acid interference
miRNA micro ribonucleic acid
shRNA small hairpin ribonucleic acid
siRNA small inhibitory ribonucleic acid
hpRNA hairpin ribonucleic acid
UTR untranslated region
PCR polymerase chain reaction
RISC RNA-induced Silencing Complex
YFP yellow fluorescent protein
SEM standard error of the mean

III. Terms

In the description and tables which follow, a number of terms are used. In order to provide a clear and consistent understanding of the specification and claims, including the scope to be given such terms, the following definitions are provided:

Pathogen: As used herein, the term "pathogen" refers to fungus of the genus *Zymoseptoria, Mycosphaerella, Puccinia, Phaeosphaeria, Rhyncosporium, Alternaria, Cercospora, Magnaporthe, Venturia,* or *Phakopsora*, which infect wheat, corn, cotton, barley, tomato, sugar beet, cucumber, rice, apple, soybean, rye, oats, triticale, melons, member of Solanum family, and other true grasses. In particular examples, a pathogen is selected from the list comprising *Zymoseptoria tritici; Puccinia triticina; Phaeosphaeria nodorum; Rhyncosporium commune; Alternaria solani; Cercospora beticola; Magnaporthe grisea; Venturia inaequalis;* and *Phakopsora pachyrhizi*. In particular examples, a pathogen is selected from the list comprising *Zymoseptoria* also referred to herein as SEPTTR and *Septoria*.

Contact (with an organism): As used herein, the term "contact with" or "uptake by" an organism (e.g., a fungal pathogen), with regard to a nucleic acid molecule, includes internalization of the nucleic acid molecule into the organism, for example and without limitation: uptake of the molecule by the organism (e.g., by feeding); contacting the organism with a composition comprising the nucleic acid molecule; and soaking of organisms with a solution comprising the nucleic acid molecule.

Encoding a dsRNA: As used herein, the term "encoding a dsRNA" includes a gene whose RNA transcription product is capable of forming an intramolecular dsRNA structure or intermolecular dsRNA structure (e.g., by hybridizing to a target RNA molecule).

Expression: As used herein, "expression" of a coding sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression.

Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern (RNA) blot, RT-PCR, western (immuno-) blot, or in vitro, in situ, or in vivo protein activity assay(s).

Genetic material: As used herein, the term "genetic material" includes all genes and nucleic acid molecules, such as DNA and RNA.

Inhibition: As used herein, the term "inhibition", when used to describe an effect on a coding sequence (for example, a gene), refers to a measurable decrease in the cellular level of mRNA transcribed from the coding sequence and/or peptide, polypeptide, or protein product of the coding sequence. In some examples, expression of a coding sequence may be inhibited such that expression is approximately eliminated. "Specific inhibition" refers to the inhibition of a target coding sequence without consequently affecting expression of other coding sequences (e.g., genes) in the cell wherein the specific inhibition is being accomplished.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. By convention, the nucleotide sequence of a nucleic acid molecule is read from the 5' to the 3' end of the molecule. The "complement" of a nucleotide sequence refers to the sequence, from 5' to 3', of the nucleobases which form base pairs with the nucleobases of the nucleotide sequence (i.e., A-T/U, and G-C). The "reverse complement" of a nucleic acid sequence refers to the sequence, from 3' to 5', of the nucleobases which form base pairs with the nucleobases of the nucleotide sequence.

Some embodiments include nucleic acids comprising a template DNA that is transcribed into an RNA molecule that is the complement of an mRNA molecule. In these embodiments, the complement of the nucleic acid transcribed into the mRNA molecule is present in the 5' to 3' orientation, such that RNA polymerase (which transcribes DNA in the 5' to 3' direction) will transcribe a nucleic acid from the complement that can hybridize to the mRNA molecule. Unless explicitly stated otherwise, or it is clear to be otherwise from the context, the term "complement" therefore refers to a polynucleotide having nucleobases, from 5' to 3', that may form base pairs with the nucleobases of a reference nucleic acid. Similarly, unless it is explicitly stated to be otherwise (or it is clear to be otherwise from the context), the "reverse complement" of a nucleic acid refers to the complement in reverse orientation. The foregoing is demonstrated in the following illustration:

```
ATGATGATG polynucleotide

TACTACTAC "complement" of the polynucleotide

CATCATCAT "reverse complement" of the
polynucleotide
```

"Nucleic acid molecules" include single- and double-stranded forms of DNA (ssDNA and dsDNA, respectively); single-stranded forms of RNA (ssRNA); and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), shRNA (small hairpin RNA), miRNA (micro-RNA), hpRNA (hairpin RNA), tRNA (transfer RNA, whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "polynucleotide" and "nucleic acid" and "fragments" thereof, or more generally "segment", will be understood by those in the art as a functional term that includes both genomic sequences, ribosomal RNA sequences, transfer RNA sequences, messenger RNA sequences, operon sequences, and smaller engineered nucleotide sequences that encode or may be adapted to encode peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of DNA and RNA (reverse transcribed into a cDNA) sequences. In PCR, the oligonucleotide is typically referred to as a "primer", which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding sequence", "structural nucleotide sequence", or "structural nucleic acid molecule" refers to a nucleotide sequence that is ultimately translated into a polypeptide, via transcription and mRNA, when placed under the control of appropriate regulatory sequences. With respect to RNA, the term "coding polynucleotide" refers to a polynucleotide that is translated into a peptide, polypeptide, or protein. Coding polynucleotides include, but are not limited to: genomic DNA; cDNA; EST; and recombinant nucleotide sequences. The boundaries of a coding sequence are determined by a translation start codon at the 5'-terminus and a translation stop codon at the 3'-terminus. Although a translation initiation codon can be 5'-AUG (in transcribed mRNA molecules; 5'-ATG in the corresponding DNA molecule), some genes, including mitochondrial genes, have a translation start codon having the RNA sequence 5'-GUG, 5'-UUG or 5'-CUG, 5'-AUA, 5'-ACG or 5'-CUG. Thus, the terms "translation initiation codon" and "start codon" can encompass many codon sequences. It is also known that eukaryotic and prokaryotic genes may have two or more alternative start codons, any one of which may be utilized for translation initiation in a particular cell type or tissue, or under a particular set of conditions. Therefore, "start codon" and "translation initiation codon" refer to the codon or codons that are used to initiate translation of an mRNA molecule transcribed from a gene, such as a mitochondrial gene, regardless of the sequence(s) of such codons. Similarly, "stop codon" and "translation termination codon" refer to the codon or codons that are used to terminate translation of an mRNA molecule transcribed from a gene, such as a mitochondrial gene, regardless of the sequence(s) of such codons.

As used herein, "transcribed non-coding polynucleotide" refers to at least one segment of an mRNA molecule such as 5'UTR, 3'UTR, and intron segments that are not translated into a peptide, polypeptide, or protein. Further, "transcribed non-coding polynucleotide" refers to a nucleic acid that is transcribed into an RNA that functions in the cell, for example, structural RNAs (e.g., ribosomal RNA (rRNA) as exemplified by 5S rRNA, 5.8S rRNA, 16S rRNA, 18S rRNA, 23S rRNA, and 28S rRNA, and the like); transfer RNA (tRNA); and snRNAs such as U4, U5, U6, and the like. Transcribed non-coding polynucleotides also include, for example and without limitation, small RNAs (sRNA), which term is often used to describe small bacterial non-coding RNAs; small nucleolar RNAs (snoRNA); microRNAs; small interfering RNAs (siRNA); Piwi-interacting RNAs (piRNA); and long non-coding RNAs. Further still, "transcribed non-coding polynucleotide" refers to a polynucleotide that may natively exist as an intragenic "linker" in a nucleic acid and which is transcribed into an RNA molecule.

Genome: As used herein, the term "genome" refers to chromosomal DNA found within the nucleus of a cell, and also refers to organelle DNA found within subcellular components of the cell. In some embodiments of the disclosure, a DNA molecule may be introduced into a plant cell such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome" as it applies to bacteria refers to both the chromosome and plasmids within the bacterial cell. In some embodiments of the disclosure, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity", as used herein in the context of two nucleic acid or polypeptide sequences, refers to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-244; Higgins and Sharp (1989) CABIOS 5:151-153; Corpet et al. (1988) Nucleic Acids Res. 16:10881-10890; Huang et al. (1992) Comp. Appl. Biosci. 8:155-165; Pearson et al. (1994) Methods Mol. Biol. 24:307-331; Tatiana et al. (1999) FEMS Microbiol. Lett. 174:247-250. A detailed consideration of sequence alignment methods and homology calculations can be found in, e.g., Altschul et al. (1990) J. Mol. Biol. 215:403-410.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization will determine the stringency of hybridization. The ionic strength of the wash buffer and the wash temperature also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11, and updates; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, NY, 1993; and Ausubel et al., Eds., *Current Protocols in Molecular Biology*, Chapter 2, Greene Publishing and Wiley-Interscience, NY, 1995, and updates.

As used herein, "stringent conditions" encompass conditions under which hybridization will occur only if there is more than 80% sequence match between the hybridization molecule and a homologous sequence within the target nucleic acid molecule. "Stringent conditions" include further particular levels of stringency. Thus, as used herein, "moderate stringency" conditions are those under which molecules with more than 80% sequence match (i.e. having less than 20% mismatch) will hybridize; conditions of "high stringency" are those under which sequences with more than 90% match (i.e. having less than 10% mismatch) will hybridize; and conditions of "very high stringency" are those under which sequences with more than 95% match (i.e. having less than 5% mismatch) will hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

Moderate Stringency condition (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology", with regard to a contiguous nucleic acid sequence, refers to contiguous nucleotide sequences that are borne by nucleic acid molecules that hybridize under stringent conditions to a nucleic acid molecule having the reference nucleic acid sequence. For example, nucleic acid molecules having sequences that are substantially homologous to a reference nucleic acid sequence of SEQ ID NO:1 are those nucleic acid molecules that hybridize under stringent conditions (e.g., the Moderate Stringency conditions set forth, supra) to nucleic acid molecules having the reference nucleic acid sequence of SEQ ID NO:1. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" refers to a gene in two or more species that has evolved from a common ancestral nucleotide sequence, and may retain the same function in the two or more species.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

Wheat plant: As used herein the term "wheat" or "wheat plant" refers to a plant of the genus, *Triticum*, for example, *T. aestivum, T. aethiopicum, T. araraticum, T. boeoticum, T. carthlicum, T. compactum, T. dicoccoides, T. dicoccon, T. durum, T. ispahanicum, T. karamyschevii, T. macha, T. militinae, T. monococcum, T. polonicum, T. spelta, T. sphaerococcum, T. timopheevii, T. turanicum, T. turgidum, T. urartu, T. vavilovii, T. zhukovskyi.*

Unless specifically indicated or implied, the terms "a", "an", and "the" signify "at least one" as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's *Genes X*, Jones & Bartlett Publishers, 2009 (ISBN 10 0763766321); Krebs et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a *Zymoseptoria* Sequence

A. Overview

Described herein are nucleic acid molecules useful for the control of pathogens. Described nucleic acid molecules include target sequences (e.g., native genes, and non-coding sequences), dsRNAs, siRNAs, hpRNAs, shRNA, and miRNAs. For example, dsRNA, siRNA, shRNA, miRNA and/or hpRNA molecules are described in some embodiments that may be specifically complementary to all or part of one or more native nucleic acid sequences in a pathogen. In these and further embodiments, the native nucleic acid sequence(s) may be one or more target gene(s), the product of which may be, for example and without limitation: involved in a metabolic process; involved in a reproductive process; or involved in detoxification. Nucleic acid molecules described herein, when introduced into a cell comprising at least one native nucleic acid sequence(s) to which the nucleic acid molecules are specifically complementary, may initiate RNAi in the cell, and consequently reduce or eliminate expression of the native nucleic acid sequence(s). In some examples, reduction or elimination of the expression of a target gene by a nucleic acid molecule comprising a sequence specifically complementary thereto may be lethal in pathogens, or result in reduced growth and/or reproduction.

In some embodiments, at least one target gene in a pathogen may be selected, wherein the target gene comprises a nucleotide sequence comprising CytB (SEQ ID NO:1 or SEQ ID NO:3), or a fragment thereof (e.g., SEQ ID NOs: 4-10). In particular examples, a target gene in a pathogen is selected, wherein the target gene comprises a novel nucleotide sequence comprising CytB (SEQ ID NO:1 or SEQ ID NO:3) or a fragment thereof (e.g., SEQ ID NOs: 4-10).

In some embodiments, a target gene may be a nucleic acid molecule comprising a nucleotide sequence that encodes a polypeptide comprising a contiguous amino acid sequence that is at least 85% identical (e.g., about 90%, about 95%, about 96%, about 97%, about 98%, about 99%, about 100%, or 100% identical) to the amino acid sequence of a protein product of CytB (SEQ ID NO:1 or SEQ ID NO:3). A target gene may be any nucleic acid sequence in a pathogen, the post-transcriptional inhibition of which has a deleterious effect on the pathogen, or provides a protective benefit against the pathogen to a plant. In particular examples, a target gene is a nucleic acid molecule comprising a nucleotide sequence that encodes a polypeptide comprising a contiguous amino acid sequence that is at least 85% identical, about 90% identical, about 95% identical, about 96% identical, about 97% identical, about 98% identical, about 99% identical, about 100% identical, or 100% identical to the amino acid sequence of a protein product of novel nucleotide sequence SEQ ID NO:1 or SEQ ID NO:3.

Provided according to the disclosure are nucleotide sequences, the expression of which results in an RNA molecule comprising a nucleotide sequence that is specifically complementary to all or part of a native RNA molecule that is encoded by a coding sequence in a pathogen. In some embodiments, after uptake and/or contact of the expressed RNA molecule by a pathogen, down-regulation of the coding sequence in cells of the pathogen may be obtained. In particular embodiments, down-regulation of the coding sequence in cells of the pathogen may result in a deleterious effect on the growth, viability, proliferation, and/or reproduction of the pathogen.

In some embodiments, target sequences include transcribed non-coding RNA sequences, such as 5'UTRs; 3'UTRs; spliced leader sequences; intron sequences; outron sequences (e.g., 5'UTR RNA subsequently modified in trans splicing); donatron sequences (e.g., non-coding RNA required to provide donor sequences for trans splicing); and other non-coding transcribed RNA of target pathogen genes. Such sequences may be derived from both mono-cistronic and poly-cistronic genes.

Thus, also described herein in connection with some embodiments are iRNA molecules (e.g., dsRNAs, siRNAs, shRNA, miRNAs and hpRNAs) that comprise at least one nucleotide sequence that is specifically complementary to all or part of a target sequence in a pathogen. In some embodiments an iRNA molecule may comprise nucleotide sequence(s) that are complementary to all or part of a plurality of target sequences; for example, 2, 3, 4, 5, 6, 7, 8, 9, 10, or more target sequences. Also disclosed are cDNA sequences that may be used for the production of dsRNA molecules, siRNA molecules, shRNA molecules, miRNA molecules and/or hpRNA molecules that are specifically complementary to all or part of a target sequence in a pathogen.

In some embodiments, nucleic acid molecules useful for the control of pathogens may include: all or part of a native nucleic acid sequence isolated from *Zymoseptoria* comprising CytB (SEQ ID NO:1 or SEQ ID NO:3); nucleotide sequences that when expressed result in an RNA molecule comprising a nucleotide sequence that is specifically complementary to all or part of a native RNA molecule that is encoded by CytB (SEQ ID NO:1 or SEQ ID NO:3); iRNA molecules (e.g., dsRNAs, siRNAs, shRNA, miRNAs and hpRNAs) that comprise at least one nucleotide sequence that is specifically complementary to all or part of CytB (SEQ ID NO:1 or SEQ ID NO:3); cDNA sequences that may be used for the production of dsRNA molecules, siRNA molecules, shRNA molecules, miRNA and/or hpRNA molecules that are specifically complementary to all or part of CytB (SEQ ID NO:1 or SEQ ID NO:3); and recombinant DNA constructs.

B. Nucleic Acid Molecules

The present disclosure provides, inter alia, iRNA (e.g., dsRNA, siRNA, shRNA, miRNA, and hpRNA) molecules that inhibit target gene expression in a cell or tissue of a pathogen; and DNA molecules capable of being expressed as an iRNA molecule in a cell or microorganism to inhibit target gene expression in a cell or tissue of a pathogen.

Some embodiments of the disclosure provide an isolated nucleic acid molecule comprising at least one (e.g., one, two, three, or more) nucleotide sequence(s) selected from the group consisting of: SEQ ID NO:1; the complement of SEQ ID NO:1; SEQ ID NO:3; the complement of SEQ ID NO:3; a fragment of at least 15 contiguous nucleotides (e.g., 15, 16, 17, 18, 19, 20, 21, 22, 23, 24, 25, 26, 27, 28, 29, 30 or more contiguous nucleotides) of any of SEQ ID NO:1 and SEQ ID NO:3 (e.g., SEQ ID NOs: 4-10); the complement of a fragment of at least 15 contiguous nucleotides of any of SEQ ID NO:1 and SEQ ID NO:3; a native coding sequence of a pathogenic organism (e.g., *Zymoseptoria*) comprising all or part of any of SEQ ID NO:1 and SEQ ID NO:3; the complement of a native coding sequence of a pathogenic organism comprising all or part of any of SEQ ID NO:1 and SEQ ID NO:3; a native non-coding sequence of a pathogenic organism that is transcribed into a native RNA molecule comprising all or part of any of SEQ ID NO:1 and SEQ ID NO:3; the complement of a native non-coding sequence of a pathogenic organism that is transcribed into a native RNA molecule comprising all or part of any of SEQ ID NO:1 and SEQ ID NO:3; a fragment of at least 15 contiguous nucleotides of a native non-coding sequence of a pathogenic organism that is transcribed into a native RNA molecule comprising all or part of any of SEQ ID NO:1 and SEQ ID NO:3; the complement of a fragment of at least 15 contiguous nucleotides of a native non-coding sequence of a pathogenic organism that is transcribed into a native RNA molecule comprising all or part of any of SEQ ID NO:1 and SEQ ID NO:3; a fragment of at least 15 contiguous nucleotides of a native coding sequence of a pathogenic organism that is transcribed into a native RNA molecule comprising SEQ ID NO:1 and SEQ ID NO:3; the complement of a fragment of at least 15 contiguous nucleotides of a native coding sequence of a pathogenic organism that is transcribed into a native RNA molecule comprising SEQ ID NO:1 and SEQ ID NO:3. In some embodiments of the disclosure, the isolated nucleic acid molecule comprises one or more of SEQ ID NOs: 4-10. In particular embodiments, contact with or uptake by a fungal pathogen of the isolated nucleic acid sequence inhibits the growth, development, reproduction and/or feeding of the pathogen.

In some embodiments, a nucleic acid molecule of the disclosure may comprise at least one (e.g., one, two, three, or more) DNA sequence(s) capable of being expressed as an iRNA molecule in a cell or microorganism to inhibit target gene expression in a cell or tissue of a pathogen. In one embodiment, the at least one (e.g., one, two, three, or more) DNA sequence(s) may be derived from a polynucleotide(s) selected from the group consisting of: SEQ ID NO:1 and SEQ ID NO:3. Derivatives of SEQ ID NO:1 or SEQ ID NO:3 include fragments of SEQ ID NO:1 or SEQ ID NO:3. In some embodiments, such a fragment may comprise, for example, at least about 15 contiguous nucleotides of SEQ ID NO:1 or SEQ ID NO:3, or a complement thereof. Thus, such a fragment may comprise, for example, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200 or more contiguous nucleotides of SEQ ID NO:1 or SEQ ID NO:3, or a complement thereof. In these and further embodiments, such a fragment may comprise, for example, more than about 15 contiguous nucleotides of SEQ ID NO:1 or SEQ ID NO:3, or a complement thereof. Thus, a fragment of SEQ ID NO:1 or SEQ ID NO:3 may comprise, for example, 15, 16, 17, 18, 19, 20, 21, about 25, (e.g., 22, 23, 24, 25, 26, 27, 28, and 29), about 30, about 40, (e.g., 35, 36, 37, 38, 39, 40, 41, 42, 43, 44, and 45), about 50, about 60, about 70, about 80, about 90, about 100, about 110, about 120, about 130, about 140, about 150, about 160, about 170, about 180, about 190, about 200 or more contiguous nucleotides of SEQ ID NO:1 or SEQ ID NO:3, or a complement thereof. In some specific embodiments the fragment is selected from the group consisting of SEQ ID NOs: 4-10.

Some embodiments comprise introducing partial- or fully-stabilized dsRNA molecules into a pathogen to inhibit expression of a target gene in a cell or tissue of the pathogen. When expressed as an iRNA molecule (e.g., dsRNA, siRNA, shRNA, miRNA, and hpRNA) and taken up by a pathogen, nucleic acid sequences comprising one or more fragments of SEQ ID NO:1 or SEQ ID NO:3 (e.g., SEQ ID NOs: 4-10) may cause one or more of death, growth inhibition, reduction in population size, and/or cessation of infection by a pathogen. For example, in some embodiments, a dsRNA molecule comprising a nucleotide sequence including about 15 to about 300 or about 19 to about 300 nucleotides that are substantially homologous to a pathogen target gene sequence and comprising one or more fragments of a nucleotide sequence comprising SEQ ID NO:1 or SEQ ID NO:3 is provided. Expression of such a dsRNA molecule may, for example, lead to mortality and/or growth inhibition in a pathogen that takes up the dsRNA molecule.

In certain embodiments, dsRNA molecules provided by the disclosure comprise nucleotide sequences complementary to a target gene comprising SEQ ID NO:1 or SEQ ID NO:3 and/or nucleotide sequences complementary to a fragment of SEQ ID NO:1 or SEQ ID NO:3, the inhibition of which target gene in a pathogen results in the reduction or removal of a protein or nucleotide sequence agent that is essential for the pathogen's growth, development, or other biological function. A selected nucleotide sequence may exhibit from about 80% to about 100% sequence identity to SEQ ID NO:1 or SEQ ID NO:3, a contiguous fragment of the nucleotide sequence set forth in SEQ ID NO:1 or SEQ ID NO:3, or the complement of either of the foregoing. For example, a selected nucleotide sequence may exhibit about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; or about 100% sequence identity to SEQ ID NO:1 or SEQ ID NO:3, a contiguous fragment of the nucleotide sequence set forth in SEQ ID NO:1 or SEQ ID NO:3, or the complement of either of the foregoing.

In some embodiments, a DNA molecule capable of being expressed as an iRNA molecule in a cell or microorganism to inhibit target gene expression may comprise a single nucleotide sequence that is specifically complementary to all or part of a native nucleic acid sequence found in one or more target pathogen species, or the DNA molecule can be constructed as a chimera from a plurality of such specifically complementary sequences.

dsRNA nucleic acid molecules comprise double strands of polymerized ribonucleotide sequences, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNase III enzyme, such as DICER in eukaryotes, either in vitro or in vivo. See Elbashir et al. (2001) Nature 411:494-498; and Hamilton and Baulcombe (1999) Science 286(5441):950-952. DICER or functionally-equivalent RNase III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNase III enzymes are unwound and separated into single-stranded RNA in the cell. The siRNA molecules then specifically hybridize with RNA sequences transcribed from a target gene, and both RNA molecules are subsequently degraded by an inherent cellular RNA-degrading mechanism. This process may result in the effective degradation or removal of the RNA sequence encoded by the target gene in the target organism. The outcome is the post-transcriptional silencing of the targeted gene. In some embodiments, siRNA molecules produced by endogenous RNase III enzymes from heterologous nucleic acid molecules may efficiently mediate the down-regulation of target genes in pathogens.

C. Obtaining Nucleic Acid Molecules

A variety of native sequences in pathogens may be used as target sequences for the design of nucleic acid molecules of the disclosure, such as iRNAs and DNA molecules encoding iRNAs. Selection of native sequences is not, however, a straight-forward process. Only a small number of native sequences in the pathogen will be effective targets. For example, it cannot be predicted with certainty whether a particular native sequence can be effectively down-regulated by nucleic acid molecules of the disclosure, or whether down-regulation of a particular native sequence will have a detrimental effect on the growth, viability, proliferation, and/or reproduction of the pathogen.

In some embodiments, nucleic acid molecules of the disclosure are selected to target cDNA sequences that encode proteins or parts of proteins essential for pathogen survival, such as amino acid sequences involved in metabolic or catabolic biochemical pathways, cell division, reproduction, energy metabolism, digestion, host plant recognition, and the like. As described herein, uptake or contact of compositions by a target organism containing one or more dsRNAs, at least one segment of which is specifically complementary to at least a substantially identical segment of RNA produced in the cells of the target organism, can result in the death or other inhibition of the target. A nucleotide sequence, either DNA or RNA, derived from a pathogen can be used to construct formulations to protect plants from infection by the pathogen. The host plant of the pathogen (e.g., wheat), for example, can be treated with one or more of the nucleotide sequences derived from the pathogen as provided herein. This may result in the suppression of expression of one or more genes in the cells of the pathogen, and ultimately death or inhibition of its growth or development.

Thus, in some embodiments, a gene is targeted that is essentially involved in the growth, development, and reproduction of a pathogen. Other target genes for use in the present disclosure may include, for example, those that play roles in pathogen viability, growth, development, infectivity, and reproduction. A target gene may therefore be a housekeeping gene or a transcription factor. Additionally, a native pathogen nucleotide sequence for use in the present disclosure may also be derived from a homolog (e.g., an ortholog), of a plant, viral, bacterial or insect gene, the function of which is known to those of skill in the art, and the nucleotide sequence of which is specifically hybridizable with a target gene in the genome of the target pathogen. Methods of identifying a homolog of a gene with a known nucleotide sequence by hybridization are known to those of skill in the art.

In some embodiments, the disclosure provides methods for obtaining a nucleic acid molecule comprising a nucleotide sequence for producing an iRNA (e.g., dsRNA, siRNA, shRNA, miRNA, and hpRNA) molecule. One such embodiment comprises: (a) analyzing one or more target gene(s) for their expression, function, and phenotype upon dsRNA-mediated gene suppression in a pathogen; (b) probing a cDNA or gDNA library with a probe comprising all or a portion of a nucleotide sequence or a homolog thereof from a targeted pathogen that displays an altered (e.g., reduced) growth or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA sequence or a homolog thereof; and (f) chemically synthesizing all or a substantial portion of a gene sequence, or a siRNA or miRNA or shRNA or hpRNA or mRNA or dsRNA.

In further embodiments, a method for obtaining a nucleic acid fragment comprising a nucleotide sequence for producing a substantial portion of an iRNA (e.g., dsRNA, siRNA, shRNA, miRNA, and hpRNA) molecule includes: (a) synthesizing first and second oligonucleotide primers specifically complementary to a portion of a native nucleotide sequence from a targeted pathogen; and (b) amplifying a cDNA or gDNA insert present in a cloning vector using the first and second oligonucleotide primers of step (a), wherein the amplified nucleic acid molecule comprises a substantial portion of a siRNA or shRNA or miRNA or hpRNA or mRNA or dsRNA molecule.

Nucleic acids of the disclosure can be isolated, amplified, or produced by a number of approaches. For example, an iRNA (e.g., dsRNA, siRNA, shRNA, miRNA, and hpRNA) molecule may be obtained by PCR amplification of a target nucleic acid sequence (e.g., a target gene or a target transcribed non-coding sequence) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P. E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,415,732, 4,458,066, 4,725,677, 4,973,679, and 4,980,460. Alternative chemistries resulting in non-natural backbone groups, such as phosphorothioate, phosphoramidate, and the like, can also be employed.

An RNA, dsRNA, siRNA, miRNA, shRNA, or hpRNA molecule of the present disclosure may be produced chemically or enzymatically by one skilled in the art through manual or automated reactions, or in vivo in a cell comprising a nucleic acid molecule comprising a sequence encoding the RNA, dsRNA, siRNA, miRNA, shRNA, or hpRNA molecule. RNA may also be produced by partial or total organic synthesis—any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of nucleotide sequences are known in the art. See, e.g., U.S. Pat. Nos. 5,593,874, 5,693,512, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the disclosure also provides a DNA molecule for introduction into a cell (e.g., a bacterial cell, a yeast cell, or a plant cell), wherein the DNA molecule comprises a nucleotide sequence that, upon expression to RNA and contact and/or uptake by a pathogen, achieves suppression of a target gene in a cell or tissue of the pathogen.

In specific embodiments, a recombinant DNA molecule of the disclosure may comprise a nucleic acid sequence encoding a dsRNA molecule. Such recombinant DNA molecules may encode dsRNA molecules capable of inhibiting the expression of endogenous target gene(s) in a pathogen cell upon contact and/or uptake.

In these and further embodiments, one strand of a dsRNA molecule may be formed by transcription from a nucleotide sequence which is substantially homologous to a nucleotide sequence consisting of SEQ ID NO:1; the complement of SEQ ID NO:1; SEQ ID NO:3, the complement of SEQ ID NO:3; a fragment of at least 19 contiguous nucleotides of SEQ ID NOs:1 or 3 (e.g., SEQ ID NOs: 4-10); the complement of a fragment of at least 19 contiguous nucleotides of SEQ ID NOs:1 or 3; a native coding sequence of a *Zymoseptoria* organism comprising SEQ ID NOs:1 or 3; the complement of a native coding sequence of a *Zymoseptoria* organism comprising SEQ ID NOs:1 or 3; a native non-coding sequence of a *Zymoseptoria* organism that is transcribed into a native RNA molecule comprising SEQ ID NOs:1 or 3; the complement of a native non-coding sequence of a *Zymoseptoria* organism that is transcribed into a native RNA molecule comprising SEQ ID NOs:1 or 3; a fragment of at least 19 contiguous nucleotides of a native coding sequence of a *Zymoseptoria* organism comprising SEQ ID NOs:1 or 3; the complement of a fragment of at least 19 contiguous nucleotides of a native coding sequence of a *Zymoseptoria* organism comprising SEQ ID NOs:1 or 3; a fragment of at least 19 contiguous nucleotides of a native non-coding sequence of a *Zymoseptoria* organism that is transcribed into a native RNA molecule comprising SEQ ID NOs:1 or 3; and the complement of a fragment of at least 19 contiguous nucleotides of a native non-coding sequence of a *Zymoseptoria* organism that is transcribed into a native RNA molecule comprising SEQ ID NOs:1 or 3.

In particular embodiments, a recombinant DNA molecule encoding a dsRNA molecule may comprise at least two nucleotide sequence segments within a transcribed sequence, such sequences arranged such that the transcribed sequence comprises a first nucleotide sequence segment in a sense orientation, and a second nucleotide sequence segment (comprising the complement of the first nucleotide sequence segment) is in an antisense orientation, relative to at least one promoter, wherein the sense nucleotide sequence segment and the antisense nucleotide sequence segment are linked or connected by a spacer sequence segment of from about five (~5) to about one thousand (~1000) nucleotides. The spacer sequence segment may form a loop between the sense and antisense sequence segments. The sense nucleotide sequence segment or the antisense nucleotide sequence segment may be substantially homologous to the nucleotide sequence of a target gene (e.g., a gene comprising SEQ ID NOs:1 or 3) or fragment thereof (e.g., SEQ ID NOs: 4-10). In some embodiments, however, a recombinant DNA molecule may encode a dsRNA molecule without a spacer sequence. In embodiments, a sense coding sequence and an antisense coding sequence may be different lengths.

Sequences identified as having a deleterious effect on pathogens or a plant-protective effect with regard to pathogens may be readily incorporated into expressed dsRNA molecules through the creation of appropriate expression cassettes in a recombinant nucleic acid molecule of the disclosure. For example, such sequences may be expressed as a hairpin with stem and loop structure by taking a first segment corresponding to a target gene sequence (e.g., SEQ ID NO:1, SEQ ID NO:3, and fragments thereof (e.g., SEQ ID NOs: 4-10)); linking this sequence to a second segment spacer region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms and comprises the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native pathogen sequence is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

V. Target Gene Suppression in a Plant Pathogen

A. Overview

In some embodiments of the disclosure, at least one nucleic acid molecule useful for the control of pathogens may be provided to a pathogen, wherein the nucleic acid molecule leads to RNAi-mediated gene silencing in the pathogen. In particular embodiments, an iRNA molecule (e.g., dsRNA, siRNA, miRNA, shRNA, and hpRNA) may be provided to the pathogen. In some embodiments, a nucleic acid molecule useful for the control of pathogens may be provided to a pathogen by contacting the nucleic acid molecule with the pathogen. In these and further embodiments, a nucleic acid molecule useful for the control of pathogens may be provided by contact or on a feeding substrate of the pathogen. In these and further embodiments, a nucleic acid molecule useful for the control of pathogens may be provided through contact and/or uptake of plant material treated with the nucleic acid molecule that is contacted and/or uptaken by the pathogen.

B. RNAi-Mediated Target Gene Suppression

In embodiments, the disclosure provides iRNA molecules (e.g., dsRNA, siRNA, miRNA, shRNA, and hpRNA) that may be designed to target essential native nucleotide sequences (e.g., essential genes) in the transcriptome of a pathogen (e.g., *Zymoseptoria tritici* and *Phaeosphaeria nodorum*), for example by designing an iRNA molecule that comprises at least one strand comprising a nucleotide sequence that is specifically complementary to the target sequence. The sequence of an iRNA molecule so designed may be identical to the target sequence, or may incorporate mismatches that do not prevent specific hybridization between the iRNA molecule and its target sequence.

iRNA molecules of the disclosure may be used in methods for gene suppression in a pathogen, thereby reducing the level or incidence of damage caused by the fungal pathogen on a plant. As used herein the term "gene suppression" refers to any of the well-known methods for reducing the levels of protein produced as a result of gene transcription to mRNA and subsequent translation of the mRNA, including the reduction of protein expression from a gene or a coding sequence including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand". The passenger strand may be degraded, and the guide strand may be incorporated into RISC. Post-transcriptional inhibition occurs by specific hybridization of the guide strand with a specifically complementary sequence of an mRNA molecule, and subsequent cleavage by the enzyme, Argonaute (catalytic component of the RISC complex).

In embodiments of the disclosure, any form of iRNA molecule may be used. Those of skill in the art will understand that dsRNA molecules typically are more stable than are single-stranded RNA molecules, during preparation and during the step of providing the iRNA molecule to a cell, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a nucleotide sequence, which nucleotide sequence may be expressed in vitro to produce an iRNA molecule that is substantially homologous to a nucleic acid molecule encoded by a nucleotide sequence within the genome of a pathogen. In certain embodiments, the in vitro transcribed iRNA molecule may be a stabilized dsRNA molecule that comprises a stem-loop structure. After a pathogen contacts the in vitro transcribed iRNA molecule, post-transcriptional inhibition of a target gene in the pathogen (for example, an essential gene) may occur.

In some embodiments of the disclosure, expression of a nucleic acid molecule comprising at least 15 contiguous nucleotides of a nucleotide sequence is used in a method for post-transcriptional inhibition of a target gene in a pathogen, wherein the nucleotide sequence is selected from the group consisting of: SEQ ID NO:1; the complement of SEQ ID NO:1; SEQ ID NO:3; the complement of SEQ ID NO:3; a fragment of at least 15 contiguous nucleotides of SEQ ID NO:1 or SEQ ID NO:3 (e.g., SEQ ID NOs: 4-10); the complement of a fragment of at least 15 contiguous nucleotides of SEQ ID NO:1 or SEQ ID NO:3; a native coding sequence of a *Zymoseptoria* organism comprising SEQ ID NO:1 or SEQ ID NO:3; the complement of a native coding sequence of a *Zymoseptoria* organism comprising SEQ ID NO:1 or SEQ ID NO:3; a native non-coding sequence of a *Zymoseptoria* organism that is transcribed into a native RNA molecule comprising SEQ ID NO:1 or SEQ ID NO:3; the complement of a native non-coding sequence of a *Zymoseptoria* organism that is transcribed into a native RNA molecule comprising SEQ ID NO:1 or SEQ ID NO:3; the complement of a native non-coding sequence of a *Zymoseptoria* organism that is transcribed into a native RNA molecule comprising SEQ ID NO:1 or SEQ ID NO:3; a fragment of at least 15 contiguous nucleotides of a native coding sequence of a *Zymoseptoria* organism comprising SEQ ID NO:1 or SEQ ID NO:3; the complement of a fragment of at least 15 contiguous nucleotides of a native coding sequence of a *Zymoseptoria* organism comprising SEQ ID NO:1 or SEQ ID NO:3; a fragment of at least 15 contiguous nucleotides of a native non-coding sequence of a *Zymoseptoria* organism that is transcribed into a native RNA molecule comprising SEQ ID NO:1 or SEQ ID NO:3; and the complement of a fragment of at least 15 contiguous nucleotides of a native non-coding sequence of a *Zymoseptoria* organism that is transcribed into a native RNA molecule comprising SEQ ID NO:1 or SEQ ID NO:3. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a pathogen.

In some embodiments, expression of at least one nucleic acid molecule comprising at least 15 contiguous nucleotides of a nucleotide sequence may be used in a method for post-transcriptional inhibition of a target gene in a pathogen, wherein the nucleotide sequence is selected from the group consisting of: SEQ ID NO:1; the complement of SEQ ID NO:1; SEQ ID NO:3; the complement of SEQ ID NO:3; a fragment of at least 15 contiguous nucleotides of SEQ ID NO:1 or SEQ ID NO:3 (e.g., SEQ ID NOs: 4-10); the complement of a fragment of at least 15 contiguous nucleotides of SEQ ID NO:1 or SEQ ID NO:3; a native coding sequence of a *Zymoseptoria* organism comprising SEQ ID NO:1 or SEQ ID NO:3; the complement of a native coding sequence of a *Zymoseptoria* organism comprising SEQ ID NO:1 or SEQ ID NO:3; a native non-coding sequence of a *Zymoseptoria* organism that is transcribed into a native RNA molecule comprising SEQ ID NO:1 or SEQ ID NO:3; the complement of a native non-coding sequence of a *Zymoseptoria* organism that is transcribed into a native RNA molecule comprising SEQ ID NO:1 or SEQ ID NO:3; a fragment of at least 15 contiguous nucleotides of a native coding sequence of a *Zymoseptoria* organism comprising SEQ ID NO:1 or SEQ ID NO:3; the complement of a fragment of at least 15 contiguous nucleotides of a native coding sequence of a *Zymoseptoria* organism comprising SEQ ID NO:1 or SEQ ID NO:3; a fragment of at least 15 contiguous nucleotides of a native non-coding sequence of a *Zymoseptoria* organism that is transcribed into a native RNA molecule comprising SEQ ID NO:1 or SEQ ID NO:3; and the complement of a fragment of at least 15 contiguous nucleotides of a native non-coding sequence of a *Zymoseptoria* organism that is transcribed into a native RNA molecule comprising SEQ ID NO:1 or SEQ ID NO:3. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a pathogen. In particular examples, such a nucleic acid molecule may comprise a nucleotide sequence comprising SEQ ID NO:1 or SEQ ID NO:3.

In some embodiments of the disclosure, the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present disclosure is sequence-specific; i.e., nucleotide sequences substantially homologous to the iRNA molecule(s) are targeted for genetic inhibition. In some embodiments, an RNA molecule comprising a nucleotide sequence identical to a portion of a target gene sequence may be used for inhibition. In these and further embodiments, an RNA molecule comprising a nucleotide sequence with one or more insertion, deletion, and/or point mutations relative to a target gene sequence may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length sequence exhibiting a greater homology compensates for a longer, less homologous sequence. The length of the nucleotide sequence of a duplex region of a dsRNA molecule that is identical to a portion of a target gene transcript may be at least about 15, 16, 17, 18, 19, 20, 21, 22, 23, 24, 25, 26, 27, 28, 29, 30, 35, 40, 45, 25, 50, 100, 200, 300, 400, 500, or at least about 1000 bases. In some embodiments, a sequence of greater than 15 to 100 nucleotides may be used. In particular embodiments, a sequence of greater than about 200 to 300 nucleotides may be used. In particular embodiments, a sequence of greater than about 500 to 1000 nucleotides may be used, depending on the size of the target gene.

In certain embodiments, expression of a target gene in a pathogen may be inhibited by at least 10%; at least 33%; at least 50%; or at least 80% within a cell of the pathogen, such that a significant inhibition takes place. Significant inhibition refers to inhibition over a threshold that results in a detectable phenotype (e.g., cessation of growth, cessation of feeding, cessation of development, induced mortality, etc.), or a detectable decrease in RNA and/or gene product corresponding to the target gene being inhibited. Although in certain embodiments of the disclosure inhibition occurs in substantially all cells of the pathogen, in other embodiments inhibition occurs only in a subset of cells expressing the target gene.

In some embodiments, transcriptional suppression in a cell is mediated by the presence of a dsRNA molecule exhibiting substantial sequence identity to a promoter DNA sequence or the complement thereof, to effect what is referred to as "promoter trans suppression". Gene suppression may be effective against target genes in a pathogen that may uptake or contact such dsRNA molecules, for example, by uptaking or contacting plant material containing the dsRNA molecules. dsRNA molecules for use in promoter trans suppression may be specifically designed to inhibit or suppress the expression of one or more homologous or complementary sequences in the cells of the pathogen. Post-transcriptional gene suppression by antisense or sense oriented RNA to regulate gene expression in plant cells is disclosed in U.S. Pat. Nos. 5,107,065; 5,231,020; 5,283,184; and 5,759,829.

C. Expression of iRNA Molecules Provided to a Plant Pathogen

Expression of iRNA molecules for RNAi-mediated gene inhibition in a pathogen may be carried out in any one of many in vitro or in vivo formats. The iRNA molecules may then be provided to a pathogen, for example, by contacting the iRNA molecules with the pathogen, or by causing the pathogen to uptake or otherwise internalize the iRNA molecules. Some embodiments of the disclosure include transformed host plants of a pathogen, transformed plant cells, and progeny of transformed plants. The transformed plant cells and transformed plants may be engineered to express one or more of the iRNA molecules, for example, under the control of a heterologous promoter, to provide a protective effect. Thus, when a transgenic plant or plant cell is consumed by a pathogen during feeding, this pathogen may uptake iRNA molecules expressed in the transgenic plants or cells. The nucleotide sequences of the present disclosure may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in a pathogen comprises providing in the tissue of the host a gene-suppressive amount of at least one dsRNA molecule formed following transcription of a nucleotide sequence as described herein, at least one segment of which is complementary to an mRNA sequence within the cells of the pathogen. A dsRNA molecule, including its modified form such as an siRNA, miRNA, shRNA, or hpRNA molecule, contacted or uptaken by a pathogen in accordance with the disclosure, may be at least from about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or 100% identical to an RNA molecule transcribed from a nucleic acid molecule comprising a nucleotide sequence comprising SEQ ID NO:1 or SEQ ID NO:3. Isolated and substantially purified nucleic acid molecules including, but not limited to, non-naturally occurring nucleotide sequences and recombinant DNA constructs for providing dsRNA molecules of the present disclosure are therefore provided, which suppress or inhibit the expression of an endogenous coding sequence or a target coding sequence in the pathogen when introduced thereto.

Particular embodiments provide a delivery system for the delivery of iRNA molecules for the post-transcriptional inhibition of one or more target gene(s) in a plant pathogen and control of a population of the pathogen. In some embodiments, the delivery system comprises contact and/or uptake of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the disclosure. Transgenic plant cells and transgenic plants comprising nucleic acid sequences encoding a particular iRNA molecule may be produced by employing recombinant DNA technologies (which basic technologies are well-known in the art) to construct a plant transformation vector comprising a nucleotide sequence encoding an iRNA molecule of the disclosure (e.g., a stabilized dsRNA molecule); to transform a plant cell or plant; and to generate the transgenic plant cell or the transgenic plant that contains the transcribed iRNA molecule.

To impart pathogen resistance to a transgenic plant, a recombinant DNA molecule may, for example, be transcribed into an iRNA molecule, such as a dsRNA molecule, an siRNA molecule, an miRNA molecule, an shRNA molecule, or an hpRNA molecule. In some embodiments, an RNA molecule transcribed from a recombinant DNA molecule may form a dsRNA molecule within the tissues or fluids of the recombinant plant. Such a dsRNA molecule may be comprised in part of a nucleotide sequence that is identical to a corresponding nucleotide sequence transcribed from a DNA sequence within a pathogen of a type that may infect the host plant. Expression of a target gene within the pathogen is suppressed by the uptaken dsRNA molecule, and the suppression of expression of the target gene in the pathogen results in, for example, cessation of feeding by the pathogen, with an ultimate result being, for example, that the transgenic plant is protected from further damage by the pathogen. The modulatory effects of dsRNA molecules have been shown to be applicable to a variety of genes expressed in fungal pathogens, including, for example, endogenous genes responsible for cellular metabolism or cellular transformation, including house-keeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a nucleotide sequence for use in producing iRNA molecules may be operably linked to one or more promoter sequences functional in a plant host cell. The promoter may be an endogenous promoter, normally resident in the host genome. The nucleotide sequence of the present disclosure, under the control of an operably linked promoter sequence, may further be flanked by additional sequences that advantageously affect its transcription and/or the stability of a resulting transcript. Such sequences may be located upstream of the operably linked promoter, downstream of the 3' end of the expression construct, and may occur both upstream of the promoter and downstream of the 3' end of the expression construct.

Some embodiments provide methods for reducing the damage to a host plant (e.g., a wheat plant) caused by a pathogen that infects the plant, wherein the method comprises providing on the host plant a dsRNA comprising at least one nucleic acid molecule of the disclosure, wherein the nucleic acid molecule(s) functions upon being taken up by the pathogen to inhibit the expression of a target sequence within the pathogen, which inhibition of expression results in mortality, reduced growth, and/or reduced reproduction of the pathogen, thereby reducing the damage to the host plant caused by the pathogen. In some embodiments, the nucleic acid molecule(s) comprise dsRNA molecules. In these and further embodiments, the nucleic acid molecule(s) comprise dsRNA molecules that each comprise more than one nucleotide sequence that is specifically hybridizable to a nucleic acid molecule expressed in a pathogen cell. In some embodiments, the nucleic acid molecule(s) consist of one nucleotide sequence that is specifically hybridizable to a nucleic acid molecule expressed in a pathogen cell.

In other embodiments, a method for improving the yield of a wheat crop is provided, wherein the method comprises introducing into a wheat plant at least one nucleic acid molecule of the disclosure; cultivating the wheat plant to allow the expression of an iRNA molecule comprising the nucleic acid sequence, wherein expression of an iRNA molecule comprising the nucleic acid sequence inhibits pathogen growth and/or pathogen damage, thereby reducing or eliminating a loss of yield due to pathogen infection. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a pathogen cell. In some embodiments, the nucleic acid molecule(s) consists of one nucleotide sequence that is specifically hybridizable to a nucleic acid molecule expressed in a pathogen cell.

In some embodiments, a method for modulating the expression of a target gene in a pathogen is provided, the method comprising: transforming a plant cell with a vector comprising a nucleic acid sequence encoding at least one nucleic acid molecule of the disclosure, wherein the nucleotide sequence is operatively-linked to a promoter and a transcription termination sequence; culturing the transformed plant cell under conditions sufficient to allow for development of a plant cell culture including a plurality of transformed plant cells; selecting for transformed plant cells that have integrated the nucleic acid molecule into their genomes; screening the transformed plant cells for expression of an iRNA molecule encoded by the integrated nucleic acid molecule; selecting a transgenic plant cell that expresses the iRNA molecule; and feeding the selected transgenic plant cell to the pathogen. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a pathogen cell. In some embodiments, the nucleic acid molecule(s) consists of one nucleotide sequence that is specifically hybridizable to a nucleic acid molecule expressed in a pathogen cell. In other embodiments, a vector can comprise at least one strand of a double-stranded nucleic acid.

iRNA molecules of the disclosure can be incorporated within parts of a plant. For example, iRNA molecules can be incorporated within the seeds of a plant species (e.g., wheat), either as a product of expression from a recombinant gene incorporated into a genome of the plant cells, or as incorporated into a coating or seed treatment that is applied to the seed before planting. Alternatively, naked dsRNA and/or a plasmid expressing a dsRNA hairpin or equivalent can be incorporated within a plant part (e.g., a seed). iRNA molecules, naked dsRNA, and/or a plasmid expressing a dsRNA hairpin or equivalent can be adapted for uptake by a plant part (e.g., a root system). Also included in embodiments of the disclosure are delivery systems for the delivery of iRNA molecules to pathogens. For example, the iRNA molecules of the disclosure may be directly introduced into the cells of a pathogen. Methods for introduction may include direct mixing of iRNA with plant tissue from a host for the pathogen, as well as application of compositions comprising iRNA molecules of the disclosure to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the pathogen known to infect the plant. iRNA molecules produced by chemical or enzymatic synthesis may also be formulated in a manner consistent with common agricultural practices, and used as spray-on products for controlling plant damage by a pathogen. The formulations may include the appropriate stickers and wetters required for efficient foliar coverage, as well as UV protectants to protect iRNA molecules (e.g., dsRNA molecules) from UV damage. Such additives are commonly used in the biopestticide industry, and are well known to those skilled in the art. Such applications may be combined with other spray-on fungicide applications (biologically based or otherwise) to enhance plant protection from pathogen. Fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, *Bacillus subtilis, Bacillus subtilis* strain QST713, benalaxyl, benomyl, benthiavalicarb-isopropyl, benzylaminobenzene-sulfonate (BABS) salt, bicarbonates, biphenyl, bismerthiazol, biterta-nol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dipymetitrone, dithianon, dodemorph, dodemorph acetate, dodine, dodine free base, edifenphos, enestrobin, enestroburin, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, fluindapyr, flumorph, fluopicolide, fluopyram, fluoroimide, fluoxastrobin, fluquinconazole, flusilazole, flusulfamide, flutianil, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine, iminoctadine triacetate, iminoctadine tris(albesilate), iodocarb, ipconazole, ipfenpyrazolone, iprobenfos, iprodione, iprovalicarb, isofetamide, isoprothiolane, isopyrazam, isotianil, kasugamycin, kasugamycin hydrochloride hydrate, kresoxium-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxathiapiprolin, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, pydiflumetofen, pyrametostrobin, pyraoxystrobin, pyraziflumid, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following EXAMPLES are provided to illustrate certain particular features and/or aspects. These EXAMPLES should not be construed to limit the disclosure to the particular features or aspects described.

EXAMPLES

Example 1 dsDNA Sample Preparation

A number of dsRNA molecules (including those corresponding to CytBT1 (SEQ ID NO:4), CytBT2 (SEQ ID NO:5), and CytBT3 (SEQ ID NO:6), were synthesized and purified using a MEGASCRIPT® RNAi kit (Life Techonologies, Grand Island, N.Y.), HiScribe® T7 In Vitro Transcription Kit (New England BioLabs, Ipswich, Mass.), or proprietary methods (Genolution, Seoul, Korea). The purified dsRNA molecules were prepared in TE buffer, and all bioassays contained a control treatment consisting of this buffer, which served as a background check for curative and preventative inhibition of *Zymoseptoria*. The concentrations of dsRNA molecules in the bioassay buffer were measured using a NANODROP™ 8000 spectrophotometer (THERMO SCIENTIFIC, Wilmington, Del.). CytBT1 (SEQ ID NO:4), CytBT2 (SEQ ID NO:5), CytBT3 (SEQ ID NO:6), CytBT4 (SEQ ID NO:7), CytBT5 (SEQ ID NO:8), CytBT6 (SEQ ID NO:9), and CytBT7 (SEQ ID NO:10) were synthesized and produced by a third party manufacturer (AgroRNA, Seoul, Korea).

Example 2

Identification of Candidate Target Genes

CytB is a known fungicidal target for strobilurin fungicides. The gene and coding sequence of CytB from *Zymoseptoria tritici* was retrieved from GENBANK (Accession Number: AY247413).

A candidate target gene encoding *Zymoseptoria* CytB (SEQ ID NO:1 and SEQ ID NO:3) was identified as a gene that may lead to pathogen mortality, inhibition of growth, inhibition of development, or inhibition of reproduction.

The *Zymoseptoria* CytB sequences (SEQ ID NO:1 and SEQ ID NO:3) are related to a sequence from *Mycosphaerella graminicola* (GENBANK Accession No. AY247413.1). The *Septoria* CYTB amino acid sequence (SEQ ID NO:2) is a *Zymoseptoria tritici* protein having GENBANK Accession No. Q6X9S4.1 (100% similar; 100% identical over the homology region).

Full-length or partial clones of sequences of a *Zymoseptoria* candidate gene, herein referred to as CytB, were used to generate PCR amplicons for dsRNA synthesis.

SEQ ID NO:1 shows a 2028 bp DNA sequence of *Zymoseptoria* CytB.

SEQ ID NO:3 shows a 1167 bp RNA sequence of *Zymoseptoria* CytB mRNA.

SEQ ID NO:4 shows a 267 bp RNA sequence of *Zymoseptoria* CytBT1.

SEQ ID NO:5 shows a 203 bp RNA sequence of *Zymoseptoria* CytBT2.

SEQ ID NO:6 shows a 116 bp RNA sequence of *Zymoseptoria* CytBT3.

SEQ ID NO:7 shows a 219 bp RNA sequence of *Zymoseptoria* CytBT4.

SEQ ID NO:8 shows a 172 bp RNA sequence of *Zymoseptoria* CytBT5.

SEQ ID NO:9 shows a 258 bp RNA sequence of *Zymoseptoria* CytBT6.

SEQ ID NO:10 shows a 221 bp RNA sequence of *Zymoseptoria* CytBT7.

Example 3

Amplification of Target Genes to Produce dsRNA

Primers were designed to amplify portions of coding regions of each target gene by PCR. See Table 1. Where appropriate, a T7 phage promoter sequence (TTAATACGACTCACTATAGGGAGA; SEQ ID NO:44) was incorporated into the 5' ends of the amplified sense or antisense strands. See Table 1. Total RNA was extracted from *Zymoseptoria*, and first-strand cDNA was used as template for PCR reactions using opposing primers positioned to amplify all or part of the native target gene sequence.

TABLE 1

Primers and Primer Pairs used to amplify portions of coding regions of exemplary CytB target gene.

| | Coding Region ID | Primer ID | SEQ ID NO: | Sequence |
|---|---|---|---|---|
| Pair 1 | CytBT1 | CytBT1-F1 | 11 | GTTCTGATGATGGCAACCGC |
| | | CytBT1-R1 | 12 | AGGATTTCCTGAACCCGCTG |
| Pair 2 | CytBT2 | CytBT2-F2 | 13 | ACACGATACAGCGGGTTCAG |
| | | CytBT2-R2 | 14 | CAGGTGGAGTTTGCATAGGGT |
| Pair 3 | CytBT3 | CytBT3-F3 | 15 | TTACCTGCACGTGGGTAGAG |
| | | CytBT3-R3 | 16 | ACCCTAAGAATGCGGTTGCC |

Example 4

RNAi Constructs

Template preparation by PCR and dsRNA synthesis.

A strategy used to provide specific templates for CytB dsRNA production is shown in FIG. 1. Template DNAs intended for use in CytB dsRNA synthesis were prepared by PCR using the primer pairs in Table 1 and (as PCR template)

first-strand cDNA prepared from total RNA isolated from *Zymoseptoria tritici*. For each selected CytB target gene region, PCR amplifications introduced a T7 promoter sequence at the 5' ends of the amplified sense and antisense strands. The PCR products having a T7 promoter sequence at their 5' ends of both sense and antisense strands were used as transcription template for dsRNA production. See FIG. 1. The sequences of the dsRNA templates amplified with the particular primer pairs were: SEQ ID NO:4 (CytBT1), SEQ ID NO:5 (CytBT2), and SEQ ID NO:6 (CytBT3). Double-stranded RNA for bioassay was synthesized and purified using an AMBION® MEGASCRIPT® RNAi kit following the manufacturer's instructions (INVITROGEN). The concentrations of dsRNAs were measured using a NANODROP™ 8000 spectrophotometer (THERMO SCIENTIFIC, Wilmington, Del.).

Example 5

Efficacy of Candidate Target Genes

Synthetic dsRNA designed to inhibit target gene sequences identified in EXAMPLE 2 caused inhibition of disease severity when administered to *Zymoseptoria* in bioassays. CytBT1, CytBT2, and CytBT3, were observed to control *Septoria* leaf blotch on wheat seedlings when compared to the non-treated control.

TABLE 2

Compound formulation in 4-fold dilutions (15 mL).

| dsRNA | Compound (mg) | Volume (mL) | Rate (ppm) |
| --- | --- | --- | --- |
| MgCytB | 10.01 | 15 | 501 |
| MgCytBT1 |  | 15 | 125 |
| MgCytBT2 |  | 15 | 31 |
| MgCytBT3 |  | 15 | 7.82 |
|  |  | 15 | 1.96 |
|  |  | 15 | 0.49 |

RNAi (dsRNA) fungicidal solutions were prepared in TE buffer (pH 8.0), which were then mixed with 9 volumes of phosphate buffer (pH 7.5) containing 0.1% Triton X-100. The fungicidal solutions were applied to wheat seedlings using an automated booth sprayer to run-off. All sprayed plants were allowed to air dry prior to further handling.

The following served as controls: 1% silwet in phosphate buffer control, disease pressure control (untreated), and clean plant control (negative control).

These plants were inoculated with an aqueous spore suspension of *Zymoseptoria tritici* either prior to or after fungicidal treatments. After inoculation the plants were kept in 100% relative humidity to allow spores to germinate and infect the leaves. The plants were then transferred to a greenhouse until disease developed.

TABLE 3

Results of CytB dsRNA foliar application bioassays obtained with *Zymoseptoria tritici* after 3 days curative and 1 day preventative.

| Material | Rate (ppm) | SEPTTR US-184 3DC | SEPTTR US-184 1DP | SEPTTR UK-7 3DC | SEPTTR UK-7 1DP |
| --- | --- | --- | --- | --- | --- |
| CytB | 501 | 21 | 81 | 42 | 83 |
|  | 125 | 46 | 86 | 29 | 56 |
|  | 31 | 33 | 81 | 46 | 69 |
|  | 7.82 | 0 | 74 | 25 | 72 |
|  | 1.96 | 13 | 76 | 8 | 75 |
|  | 0.49 | 25 | 76 | 0 | 72 |
| 1% Silwet Control |  | 0 | 0 | 0 | 0 |
| Disease Pressure |  | 0 | 0 | 0 | 0 |
| Clean Plant Control |  | 100 | 100 | 100 | 100 |

Replicated bioassays demonstrated that uptake of dsRNA preparations derived from CytB resulted in control of *Zymoseptoria tritici*.

Example 6

Efficacy of Target Gene Fragments

The 200 ppm rate for each treatment was prepared by adding the calculated volume of the corresponding dsRNA solution in TE buffer. Lower rates were prepared as 4-fold dilutions (50 ppm, 12.5 ppm, and 3.12 ppm). A non-target dsRNA control (YFP), a TE/phosphate buffer control, disease pressure control, and clean plant control were included.

These plants were inoculated with an aqueous spore suspension of *Zymoseptoria tritici* either prior to or after fungicidal treatments. After inoculation the plants were kept in 100% relative humidity to allow spores to germinate and infect the leaves. The plants were then transferred to a greenhouse until disease developed.

TABLE 4

List of evaluated MgCytB dsRNA tiles

| Target ID (size) | Tile Size (bp) | Location in the MgCyp51 gene [5' to 3'] (bp) | dsRNA conc. (mg/mL) | Calculated Volume (mL) containing 4 mg | Used Amount (mg) |
| --- | --- | --- | --- | --- | --- |
| MgCytB* | — | — | — | — | 3.998 |
| MgCytB-T1 | 267 | 364-630 | 4.290 | 0.311 | 1.334 |
| MgCytB-T2 | 203 | 603-805 | 3.915 | 0.340 | 1.331 |
| MgCytB-T3 | 116 | 279-394 | 2.905 | 0.459 | 1.333 |
| MgCytB-T1 | 267 | 364-630 | 4.290 | 0.932 | 3.998 |
| MgCytB-T2 | 203 | 603-805 | 3.915 | 1.022 | 4.001 |
| MgCytB-T3 | 116 | 279-394 | 2.905 | 1.377 | 4.000 |

TABLE 4-continued

List of evaluated MgCytB dsRNA tiles

| | | | | | |
|---|---|---|---|---|---|
| MgCytB-T4 | 219 | 1-219 | 4.405 | 0.908 | 4.000 |
| MgCytB-T5 | 172 | 173-344 | 4.900 | 0.816 | 3.998 |
| MgCytB-T6 | 258 | 775-1032 | 5.070 | 0.789 | 4.000 |
| MgCytB-T7 | 221 | 947-1167 | 4.845 | 0.826 | 4.002 |

*MgCytB standard

| Tiles | Rate (ppm) | Average of 2 trials SEPTTR-184 3DC | Average of 2 trials SEPTTR-184 1DP | ED50 (ppm) SEPTTR-184 3DC | ED50 (ppm) SEPTTR-184 1DP | ED80 (ppm) SEPTTR-184 3DC | ED80 (ppm) SEPTTR-184 1DP | Disease Control All Rates Average (%) SEPTTR-184 3DC | Disease Control All Rates Average (%) SEPTTR-184 1DP | Sum of Disease Control (%) SEPTTR-184 3DC | Sum of Disease Control (%) SEPTTR-184 1DP |
|---|---|---|---|---|---|---|---|---|---|---|---|
| CytB* [CytBT1, 2, 3] | 200 | 82 | 73 | <3.125 | <3.125 | <3.125 | >200 | 83 | 68 | 333 | 271 |
| | 50 | 82 | 67 | | | | | | | | |
| | 12.5 | 83 | 64 | | | | | | | | |
| | 3.125 | 85 | 68 | | | | | | | | |
| MgCytB-T1 | 200 | 85 | 80 | <3.125 | <3.125 | 159 | 200 | 79 | 66 | 318 | 263 |
| | 50 | 79 | 71 | | | | | | | | |
| | 12.5 | 76 | 58 | | | | | | | | |
| | 3.125 | 77 | 53 | | | | | | | | |
| MgCytB-T2 | 200 | 90 | 77 | <3.125 | <3.125 | 27 | >200 | 82 | 71 | 329 | 285 |
| | 50 | 85 | 71 | | | | | | | | |
| | 12.5 | 77 | 71 | | | | | | | | |
| | 3.125 | 77 | 67 | | | | | | | | |
| MgCytB-T3 | 200 | 84 | 74 | <3.125 | <3.125 | <3.125 | >200 | 84 | 68 | 334 | 271 |
| | 50 | 81 | 74 | | | | | | | | |
| | 12.5 | 84 | 64 | | | | | | | | |
| | 3.125 | 84 | 59 | | | | | | | | |
| MgCytB-T4 | 200 | 83 | 74 | <3.125 | <3.125 | 44 | >200 | 79 | 73 | 316 | 292 |
| | 50 | 81 | 73 | | | | | | | | |
| | 12.5 | 75 | 74 | | | | | | | | |
| | 3.125 | 76 | 71 | | | | | | | | |
| MgCytB-T5 | 200 | 80 | 76 | 4.605 | <3.125 | 200 | >200 | 66 | 71 | 265 | 284 |
| | 50 | 72 | 73 | | | | | | | | |
| | 12.5 | 66 | 68 | | | | | | | | |
| | 3.125 | 47 | 68 | | | | | | | | |
| MgCytB-T6 | 200 | 59 | 72 | <3.125 | <3.125 | >200 | >200 | 60 | 73 | 239 | 293 |
| | 50 | 64 | 72 | | | | | | | | |
| | 12.5 | 63 | 77 | | | | | | | | |
| | 3.125 | 53 | 72 | | | | | | | | |
| MgCytB-T7 | 200 | 76 | 75 | <3.125 | <3.125 | >200 | >200 | 74 | 69 | 297 | 275 |
| | 50 | 73 | 71 | | | | | | | | |
| | 12.5 | 72 | 69 | | | | | | | | |
| | 3.125 | 76 | 60 | | | | | | | | |
| YFP | 200 | 35 | 27 | >200 | >200 | >200 | >200 | 22 | 16 | 88 | 65 |
| | 50 | 19 | 23 | | | | | | | | |
| | 12.5 | 19 | 15 | | | | | | | | |
| | 3.125 | 15 | 0 | | | | | | | | |
| Triton X-100 + buffer | | 0 | 0 | | | | | | | | |
| TE + Phosphate buffer | | 0 | 0 | | | | | | | | |
| Disease Pressure | | 0 | 0 | | | | | | | | |
| Clean Plant | | 100 | 100 | | | | | | | | |

Data from fragments shows fungicidal activity against *Zymoseptoria tritici*. The fragments prov Analysis of $T_1$ Transgenic Plants—Genomic PCR Method $T_1$ seeds of each transgenic event are kept on moist filter paper in petri plates for 3-4 days and the germinated seeds are transferred to pots. Approximately a three centimeter-long young leaf is collected from each plant and frozen dried. Genomic DNA is extracted in DNA extraction buffer containing 0.1M Tris-HCL, pH 8.0, 0.05M EDTA pH 8.0, 1.25% SDS. Primers are designed against the two extremes of the hairpin construct.

The PCR reaction is performed in a Thermalcycler with the following protocol: 95° C. for 15 min; (94° C. for 1 min; 63° C. (stargate1)/65° C. (stargate3) for 45 seconds; 72° C. for 1 min) times 35 cycles and final extension of 10 minutes at 72° C. Two amplicons are used in the study to assay for both ends of the hpRNA transgene including a large portion of the promoter.

Analysis of $T_1$ Transgenic Plants—Virus Bioassay Method

Virus inoculum is prepared by grinding wheat streak mosaic virus (WSMV) infected tissue in a mortar and pestle at a 1:10 w/v ratio in 0.02 M Potassium phosphate buffer (pH 7). The homogenate is filtered through four layers of Miracloth® (Calbiochem, USA), abrasive Celite (Johns-Manville, USA) is added at 2% w/v to a final volume of inoculum, and the mixture is left on ice for one hour. Putative transgenic BW26 plants are doubly inoculated at the 2-3 leaf stage, with the sap extracts from WSMV-infected leaf material. The sap plus celite abrasive is first applied with an air-powered spray gun and then leaves are gently rubbed with gloved fingers to ensure the infection of the plant by the virus. The plants are scored for symptoms at 14 dpi on a scale of 0-4 with 0 as healthy, 1 as mild with very few streaks, 2 as moderate with streaks that coalesce, 3 as severe with approximately 50 percent leaf area with streaks, 4 as the most severe or lethal symptoms where the streaks develop into chlorosis of more than 70 percent of leaf area. Samples are collected for WSMV-specific ELISA using Agdia reagents (Elkhart, Ind.) following manufacturer's instructions. Plates are read at A405 nm in ELISA Reader Spectra Max 340 PC (Molecular Devices, CA USA) 60 minutes after addition of substrates. Healthy controls are included on every plate, every sample is duplicated, and means are used in calculating the ELISA value ratio between inoculated and healthy controls. Data is also recorded on the fertility and height of plants.

Detection of WSMV Particles and RNA from Inoculated Transgenic Lines

Total RNA is extracted from WSMV inoculated transgenic plants using a Qiagen RNAeasy mini kit following the manufacturer's instructions. 500 ng total RNA is serially diluted in 1:10 steps to 5 pg (final dilution 10-5). In order to amplify viral RNA but avoid amplifying transcripts from the transgene, primers are designed to hybridize to sequences just outside the cloned NIa sequence used in the transgene. The primers used are NIa-1F SEQ ID NO:46 5'-CTGGACCGATCGGATTAAGA-3' and NIa-3R SEQ ID NO:47 5'-CTGAGAACTTCCATGGCACA-3'. Reverse transcription (RT) reaction is carried out at 50° C. for 30 min, following by 95° C. for 15 min; (94° C. for 1 min; 60° C. for 45 seconds; 72° C. for 1 min) times 35 cycles and final extension of 10 minutes at 72° C.

Test-Inoculation to Detect Infectious Virus in Leaf Sap

Sap is extracted from inoculated transgenic plants at 28 dpi using 0.02 M potassium phosphate buffer; the initial concentration is 1:10 (w leaf/v buffer). This is further diluted to 1:250 and 1:500 concentrations. Each dilution is mixed with celite abrasive and then inoculated onto three plants each. This method is used to evaluate the effectiveness of the hpRNA construct in eliminating viral replication and preventing the formation of infectious particles. Symptoms are scored and leaf samples collected 14 dpi for ELISA as described previously.

Segregation Analysis of NIa Transgene and Resistance in Selected $T_1$ Families

Twenty five to 35 seeds from four selected transgenic lines are germinated in pots. Leaf samples are collected and DNA is extracted as described above. Genomic PCR is carried out to detect both Stargate 1 and Stargate 3 amplicons, to ensure the presence of the complete transgene promoter and hairpin construct. In order to observe if resistance co-segregated with the transgene, the plants are inoculated with WSMV, ELISA is performed 14 dpi on inoculated plants, plant heights and symptoms are recorded. Segregation of selectable marker nptII is also determined using PCR.

Example 8

Molecular and Serological Characterization of Transgenic Wheat

An initial assessment of $T_1$ individuals will indicate the presence of the selectable marker nptII via genomic PCR, verifying that these plants are transgenic. Further analysis involves inoculating each individual plant with *Zymoseptoria* and assaying with DAS-ELISA at 14 days post inoculation (dpi). As the disease progresses affected plants will appear retarded and show a general yellow mottling. Diseased plants are usually yellowed and moderately to severely stunted with prostrated tillers often with empty spikes or spikes with shriveled kernels.

Virus accumulation in leaves is determined using ELISA and expressed as a ratio of the average ELISA value for samples from the inoculated plants relative to the ELISA value for samples from the non-inoculated controls. This is done since the ELISA value for non-inoculated controls gave a low, background reading above zero using the Agdia kit.

The RNAi Construct Conferring Immunity Against *Zymoseptoria* in Wheat

The absence of symptoms in inoculated transgenic individuals from some transgenic events will lead to the hypothesis that they are immune. Experiments are conducted to see if infectious virus or viral RNA could be recovered from resistant inoculated transgenic plants. Leaf sap from plants in four transgenic inoculated families is extracted and inoculated onto test plants of control BW26 at various dilutions to investigate the presence of any infectious disease particles.

What is claimed is:

1. A double-stranded nucleic acid comprising a ribonucleic acid (RNA) molecule that is specifically hybridizable with a polynucleotide from a phytopathogen from the genus *Zymoseptoria* selected from the group consisting of:
   SEQ ID NO:4; a complement of SEQ ID NO:4; a fragment of at least 21 contiguous nucleotides of SEQ ID NO:4;

SEQ ID NO:5; a complement of SEQ ID NO:5; a fragment of at least 21 contiguous nucleotides of SEQ ID NO:5;

SEQ ID NO:6; a complement of SEQ ID NO:6; a fragment of at least 21 contiguous nucleotides of SEQ ID NO:6; and, SEQ ID NO:7; a complement of SEQ ID NO:7; a fragment of at least 21 contiguous nucleotides of SEQ ID NO:7, wherein the double-stranded nucleic acid inhibits or down regulates the polynucleotide.

2. The double-stranded nucleic acid of claim 1, wherein the phytopathogen from the genus *Zymoseptoria* is selected from the group consisting of *Zymoseptoria tritici; Zymoseptoria citri; Zymoseptoria caryae; Zymoseptoria curcurbitacearum; Zymoseptoria dianthi; Zymoseptoria glycines; Zymoseptoria helianthi*; and *Zymoseptoria ostryae.*

3. A vector comprising at least one strand of the double-stranded nucleic acid of claim 1.

4. A double stranded oligonucleotide comprising the double stranded nucleic acid of claim 1.

5. The double-stranded oligonucleotide of claim 4, wherein the polynucleotide sequence inhibits or down regulates the expression of a CytB gene endogenous nucleotide sequence specifically complementary to the polynucleotides.

6. The double-stranded oligonucleotide of claim 4, comprising a double-stranded ribonucleic acid molecule of between about 21 to about 30 nucleotides in length.

7. A method for controlling a phytopathogen from the genus *Zymoseptoria*, the method comprising:

(a) producing a ribonucleic acid (RNA) molecule to a phytopathogen, wherein the RNA is specifically hybridizable with a polynucleotide selected from the group consisting of any of: SEQ ID NOs:4-7; the complement of any of SEQ ID NOs:4-7; a fragment of at least 21 contiguous nucleotides of any of SEQ ID NOs:4-7; the complement of a fragment of at least 21 contiguous nucleotides of any of SEQ ID NOs:4-7; a transcript of any of SEQ ID NOs:4-7; the complement of a transcript of any of SEQ ID NOs:4-7; a fragment of at least 21 contiguous nucleotides of a transcript of any of SEQ ID NOs:4-7; and the complement of a fragment of at least 21 contiguous nucleotides of a transcript of any of SEQ ID NOs:4-7;
(b) contacting the RNA molecule with the pathogen, wherein the RNA molecule is taken up by the pathogen; and,
(c) inhibiting a biological function within the pathogen, wherein the RNA molecule down regulates expression of a CytB gene endogenous nucleotide sequence.

8. The method according to claim 7, wherein the RNA molecule is double-stranded.

9. A method for controlling a phytopathogen from the genus *Zymoseptoria*, the method comprising:
providing to the phytopathogen a host plant or plant cell a pesticidal composition comprising the RNA molecule of claim 1.

10. The method according to claim 9, wherein the RNA molecule is a double-stranded ribonucleic acid molecule.

11. The method according to claim 9, wherein the pathogen is reduced relative to a population of the same pathogen infesting a host plant of the same host plant species lacking the pesticidal composition.

12. A method of controlling an infestation of a phytopathogen from the genus *Zymoseptoria* in a plant, the method comprising contacting the phytopathogen with a ribonucleic acid (RNA) molecule that is specifically hybridizable with a polynucleotide selected from the group consisting of:
SEQ ID NOs:4-7;
the complement of any of SEQ ID NOs:4-7;
a fragment of at least 21 contiguous nucleotides of any of SEQ ID NOs:4-7;
the complement of a fragment of at least 21 contiguous nucleotides of any of SEQ ID NOs:4-7;
a transcript of SEQ ID NOs:4-7;
the complement of a transcript of SEQ ID NOs:4-7;
a fragment of at least 21 contiguous nucleotides of a transcript of SEQ ID NOs:4-7; and
the complement of a fragment of at least 21 contiguous nucleotides of a transcript of SEQ ID NO:4-7.

13. The method according to claim 12, wherein contacting the phytopathogen with the RNA comprises spraying the plant with a pesticidal composition comprising the RNA.

14. The method according to claim 12, wherein the specifically hybridizable RNA is a double-stranded RNA molecule.

15. A method for improving the yield of a crop, the method comprising:
(a) applying the nucleic acid of claim 1 to a crop plant;
(b) cultivating the crop plant to introduce the double-stranded nucleic acid of claim 1, wherein the double-stranded nucleic acid inhibits reproduction or growth of a phytopathogen from the genus *Zymoseptoria*; and,
(c) harvesting the crop plant.

16. The method of claim 15, wherein the crop plant is wheat, corn, soybean, or cotton.

17. The method according to claim 15, wherein the double-stranded nucleic acid is selected from the group consisting of SEQ ID NO:4, SEQ ID NO:5, SEQ ID NO:6, SEQ ID NO:7, and the complements of any of the foregoing.

18. The method according to claim 17, wherein expression of the double-stranded nucleic acid produces an RNA molecule that suppresses a target gene in the phytopathogen that has contacted a portion of the crop plant.

19. The double-stranded nucleic acid of claim 1, further comprising a fungicide that inhibits the phytopathogen from the genus *Zymoseptoria*.

20. The double-stranded nucleic acid of claim 19, wherein the fungicide is selected from a group consisting of a strobilurin, a triazole, a carboxamid, an acylalanine, an amine, a succinate dehydrogenase inhibitor, a chlorothalonil, micronized sulphur, copper, and mixtures thereof.

21. A double-stranded RNA (dsRNA) capable of down regulating the expression of a CytB gene of a phytopathogen from the genus *Zymoseptoria* comprising a sense RNA strand and a complementary antisense RNA strand, wherein the sense RNA strand is selected from the group consisting of a polynucleotide sequence of SEQ ID NO:4, SEQ ID NO:5, SEQ ID NO:6, or SEQ ID NO:7.

22. The dsRNA of claim 21, wherein the CytB gene is selected from the group consisting of a CytB region 1, CytB region 2, CytB region 9, and CytB region T4.

23. The dsRNA of claim 21, wherein the dsRNA is applied to a plant.

24. The dsRNA of claim 23, wherein the dsRNA causes post-transcriptional gene repression or inhibition of the CytB gene in the phytopathogen infesting the plant.

25. The dsRNA of claim 21, wherein the dsRNA is formed from two separate complementary RNA sequences.

26. The dsRNA of claim 21, wherein the dsRNA is formed from a single RNA sequence with internally complementary sequences.

27. A pesticidal composition capable of inhibiting or down regulating the expression of a CytB gene in a phytopathogen from the genus *Zymoseptoria*, wherein the pesticidal composition comprises a nucleic acid of claim 1.

28. The pesticidal composition of claim 27, wherein the pesticidal composition is applied to a plant.

29. The pesticidal composition of claim 27, wherein the nucleic acid is formed from two separate complementary RNA sequences.

30. The pesticidal composition of claim 27, wherein the nucleic is formed from a single RNA sequence with internally complementary sequences.

31. The pesticidal composition of claim 27, wherein the CytB gene is selected from the group consisting of a CytB region 1, CytB region 2, CytB region 9, and CytB region T4.

32. A crop plant or plant cell cultivated by:
(a) planting a seed of the crop plant;
(b) growing the crop plant from the planted seed; and
(c) treating the crop plant or plant cell with the pesticidal composition of claim 27,
or with the double-stranded nucleic acid of claim 1.

33. The crop plant or plant cell of claim 32, wherein the crop plant comprises an agronomic trait.

34. The crop plant or plant cell of claim 33, wherein the agronomic trait is selected from the group consisting of an insecticidal resistance trait, herbicide tolerance trait, nitrogen use efficiency trait, water use efficiency trait, nutritional quality trait, RNAi trait, DNA binding trait, selectable marker trait, or any combination thereof.

35. The crop plant or plant cell of claim 33, wherein the agronomic trait comprises a transgenic trait.

36. The crop plant or plant cell of claim 32, wherein the crop plant produces a commodity product.

37. The crop plant or plant cell of claim 36, wherein the commodity product is selected from the group consisting of protein concentrate, protein isolate, grain, meal, flour, oil, or fiber.

38. The crop plant or plant cell of claim 32, wherein the crop plant is selected from the group consisting of a dicotyledonous plant or a monocotyledonous plant.

39. The crop plant or plant cell of claim 38, wherein the monocotyledonous plant is a wheat plant.

40. The crop plant or plant cell of claim 38, wherein the dicotyledonous plant is a *Glycine max* plant.

41. A plant that exhibits an improvement in fungal disease resistance, wherein the plant was topically treated with a composition that comprises:
   (a) at least one RNA of claim 1; and,
   (b) a transfer agent;
wherein the plant exhibits an improvement in fungal disease resistance that results from suppression of the CytB gene.

42. The plant of claim 41, wherein the transfer agent is an organosilicone or triton preparation.

* * * * *

SEQUENCE LISTING

```
<160> NUMBER OF SEQ ID NOS: 47

<210> SEQ ID NO 1
<211> LENGTH: 2028
```

-continued

<212> TYPE: DNA
<213> ORGANISM: Zymoseptoria tritici

<400> SEQUENCE: 1

```
ctggtaatgc aaatactggt ggaaatggcc ctactaacac tggtgccatt ggccctacta 60
acacaggttc taccggtact gctaatactg gtgctaccgc caatactaat aatgcccata 120
atcaagttca gcgtggggta ataacagatc cattggatat atacgatcct gcgggtaagt 180
tcaatagccc ttacgatcct aatgcaaaca ataaattaat ccttcatagc atagcggata 240
ctctgcaaac acgttatgat aataggaatt cttcaggagg aaatccctgt tatatttcaa 300
aaaatatatt ttccctgagc aaaagagatg gatttctgga tatttgttgt atcattatta 360
tcctgaattt tctcatcgta gcaatggagg tacgcttgat ttaacaggtt taaataatac 420
aaagtctttt agaaacaaat ttaggcgctt ttctagttag attatagtag ccttatctag 480
tttcagtaaa acttaatcga aaaaaaaaaa aaaacataat attactaaat atactcagtg 540
atgaaaaacg gttgcatgaa tattgacata tacctgactg gtatcatatt gtgtaaaacc 600
tttaataaat tgaatcttta atacacatac aaataatgag gatttggaag agtcaccctt 660
tatttagtct ggttaatggt tatcttatcg attcaccaca accaagtaat ctaagctatc 720
tatgaaattt cggttcatta ctgggatttt gtcttgtaat acaaatcgtt actggtgtta 780
cacttgctat gcattataac cctagcgtat ctgaagcatt taactcagtt gaacacataa 840
tgagagatgt aaacaatgga tgacttatac gttatcttca ctctaatact gcttcagctt 900
tcttcttttt agtttacctg cacgtgggta gagggttata ctacgggtca tacaaagccc 960
ctagaacatt aacatgaaca atcggtacta taatactagt tctgatgatg gcaaccgcat 1020
tcttagggta tgtattacct tatggtcaaa tgtctttatg aggagcaaca gttataacta 1080
acttattgag tgcaatacct tgagttggac aagacatagt tgaattcgta tgaggtggat 1140
tttctgttaa caatgcaaca ttgaacagat tctttgctct acatttcgtt ttaccgtttg 1200
tgttagctgc attagtttta atgcatctaa tagctttaca cgatacagcg ggttcaggaa 1260
atcctttagg tgtatcaggt aactacgata gattaccatt cgccccttac tttatattca 1320
aagatttaat aacaatattt ttattcatta tagtgttatc aatatttatt ttctttatgc 1380
ctaacgtttt aggtgacagc gagaattatg ttatggctaa ccctatgcaa actccacctg 1440
ctatagtgcc tgaatgatat ttattacctt tctacgctat actaagatca atacctaaca 1500
aactattagg tgtgatcgca atgttttctg ctatattgat tataatgata atgccaatta 1560
ccgatttagg tagaagtaga ggattacagt ttagaccttt aagcaagatc acattttaca 1620
tatttgttgc taacttctta gtattaatgc aattaggtgc taatcacgtt gagtcaccat 1680
ttatagaatt tgggcaaatt agtacagtac tgtacttttc acatttctta atcatagtgc 1740
ctctagtaag cttaatcgag aatactttag tggatatgca cttaaacaac acaataacgt 1800
aaaataaaaa aaaaaacttt agagatacca tcttacggaa gataaattaa attatcagtg 1860
atgatacata gtgatggtta attttttaga tgtcagctat gttacacagt tttatggtta 1920
tagttacatg atctatgtat aaaaaactaa tgtaaaacga atttctacaa tacatgtgtt 1980
catacacgaa aaataaccca agtaatatat atatattgct atatgtac 2028

<210> SEQ ID NO 2
<211> LENGTH: 388
<212> TYPE: PRT
<213> ORGANISM: Zymoseptoria tritici

```
<400> SEQUENCE: 2

Met Arg Ile Trp Lys Ser His Pro Leu Phe Ser Leu Val Asn Gly Tyr
1               5                   10                  15

Leu Ile Asp Ser Pro Gln Pro Ser Asn Leu Ser Tyr Leu Trp Asn Phe
            20                  25                  30

Gly Ser Leu Leu Gly Phe Cys Leu Val Ile Gln Ile Val Thr Gly Val
        35                  40                  45

Thr Leu Ala Met His Tyr Asn Pro Ser Val Ser Glu Ala Phe Asn Ser
    50                  55                  60

Val Glu His Ile Met Arg Asp Val Asn Asn Gly Trp Leu Ile Arg Tyr
65                  70                  75                  80

Leu His Ser Asn Thr Ala Ser Ala Phe Phe Phe Leu Val Tyr Leu His
                85                  90                  95

Val Gly Arg Gly Leu Tyr Tyr Gly Ser Tyr Lys Ala Pro Arg Thr Leu
            100                 105                 110

Thr Trp Thr Ile Gly Thr Ile Ile Leu Val Leu Met Met Ala Thr Ala
        115                 120                 125

Phe Leu Gly Tyr Val Leu Pro Tyr Gly Gln Met Ser Leu Trp Gly Ala
    130                 135                 140

Thr Val Ile Thr Asn Leu Leu Ser Ala Ile Pro Trp Val Gly Gln Asp
145                 150                 155                 160

Ile Val Glu Phe Val Trp Gly Gly Phe Ser Val Asn Asn Ala Thr Leu
                165                 170                 175

Asn Arg Phe Phe Ala Leu His Phe Val Leu Pro Phe Val Leu Ala Ala
            180                 185                 190

Leu Val Leu Met His Leu Ile Ala Leu His Asp Thr Ala Gly Ser Gly
        195                 200                 205

Asn Pro Leu Gly Val Ser Gly Asn Tyr Asp Arg Leu Pro Phe Ala Pro
    210                 215                 220

Tyr Phe Ile Phe Lys Asp Leu Ile Thr Ile Phe Leu Phe Ile Ile Val
225                 230                 235                 240

Leu Ser Ile Phe Ile Phe Phe Met Pro Asn Val Leu Gly Asp Ser Glu
                245                 250                 255

Asn Tyr Val Met Ala Asn Pro Met Gln Thr Pro Pro Ala Ile Val Pro
            260                 265                 270

Glu Trp Tyr Leu Leu Pro Phe Tyr Ala Ile Leu Arg Ser Ile Pro Asn
        275                 280                 285

Lys Leu Leu Gly Val Ile Ala Met Phe Ser Ala Ile Leu Ile Ile Met
    290                 295                 300

Ile Met Pro Ile Thr Asp Leu Gly Arg Ser Arg Gly Leu Gln Phe Arg
305                 310                 315                 320

Pro Leu Ser Lys Ile Thr Phe Tyr Ile Phe Val Ala Asn Phe Leu Val
                325                 330                 335

Leu Met Gln Leu Gly Ala Asn His Val Glu Ser Pro Phe Ile Glu Phe
            340                 345                 350

Gly Gln Ile Ser Thr Val Leu Tyr Phe Ser His Phe Leu Ile Ile Val
        355                 360                 365

Pro Leu Val Ser Leu Ile Glu Asn Thr Leu Val Asp Met His Leu Asn
    370                 375                 380

Asn Thr Ile Thr
385

<210> SEQ ID NO 3
```

```
<211> LENGTH: 1167
<212> TYPE: DNA
<213> ORGANISM: Zymoseptoria tritici

<400> SEQUENCE: 3
atgaggattt ggaagagtca ccctttattt agtctggtta atggttatct tatcgattca      60
ccacaaccaa gtaatctaag ctatctatga aatttcggtt cattactggg attttgtctt     120
gtaatacaaa tcgttactgg tgttacactt gctatgcatt ataaccctag cgtatctgaa     180
gcatttaact cagttgaaca cataatgaga gatgtaaaca atggatgact tatacgttat     240
cttcactcta atactgcttc agctttcttc tttttagttt acctgcacgt gggtagaggg     300
ttatactacg ggtcatacaa agcccctaga acattaacat gaacaatcgg tactataata     360
ctagttctga tgatggcaac cgcattctta gggtatgtat taccttatgg tcaaatgtct     420
ttatgaggag caacagttat aactaactta ttgagtgcaa taccttgagt tggacaagac     480
atagttgaat tcgtatgagg tggatttttct gttaacaatg caacattgaa cagattcttt     540
gctctacatt tcgttttacc gtttgtgtta gctgcattag ttttaatgca tctaatagct     600
ttacacgata cagcgggttc aggaaatcct ttaggtgtat caggtaacta cgatagatta     660
ccattcgccc cttactttat attcaaagat ttaataacaa tattttttatt cattatagtg     720
ttatcaatat ttattttctt tatgcctaac gttttaggtg acagcgagaa ttatgttatg     780
gctaacccta tgcaaactcc acctgctata gtgcctgaat gatatttatt accttctac     840
gctatactaa gatcaatacc taacaaacta ttaggtgtga tcgcaatgtt ttctgctata     900
ttgattataa tgataatgcc aattaccgat ttaggtagaa gtagaggatt acagtttaga     960
cctttaagca agatcacatt ttacatattt gttgctaact tcttagtatt aatgcaatta    1020
ggtgctaatc acgttgagtc accatttata gaatttgggc aaattagtac agtactgtac    1080
ttttcacatt tcttaatcat agtgcctcta gtaagcttaa tcgagaatac tttagtggat    1140
atgcacttaa acaacacaat aacgtaa                                       1167

<210> SEQ ID NO 4
<211> LENGTH: 267
<212> TYPE: DNA
<213> ORGANISM: Zymoseptoria tritici

<400> SEQUENCE: 4
gttctgatga tggcaaccgc attcttaggg tatgtattac cttatggtca aatgtcttta      60
tgaggagcaa cagttataac taacttattg agtgcaatac cttgagttgg acaagacata     120
gttgaattcg tatgaggtgg attttctgtt aacaatgcaa cattgaacag attctttgct     180
ctacatttcg ttttaccgtt tgtgttagct gcattagttt taatgcatct aatagcttta     240
cacgatacag cgggttcagg aaatcct                                         267

<210> SEQ ID NO 5
<211> LENGTH: 203
<212> TYPE: DNA
<213> ORGANISM: Zymoseptoria tritici

<400> SEQUENCE: 5
acacgataca gcgggttcag gaaatccttt aggtgtatca ggtaactacg atagattacc      60
attcgcccct tactttatat tcaaagattt aataacaata ttttattca ttatagtgtt     120
atcaatattt attttcttta tgcctaacgt tttaggtgac agcgagaatt atgttatggc     180
taaccctatg caaactccac ctg                                             203
```

<210> SEQ ID NO 6
<211> LENGTH: 116
<212> TYPE: DNA
<213> ORGANISM: Zymoseptoria tritici

<400> SEQUENCE: 6

```
ttacctgcac gtgggtagag ggttatacta cgggtcatac aaagccccta gaacattaac      60
atgaacaatc ggtactataa tactagttct gatgatggca accgcattct tagggt         116
```

<210> SEQ ID NO 7
<211> LENGTH: 219
<212> TYPE: DNA
<213> ORGANISM: Zymoseptoria tritici

<400> SEQUENCE: 7

```
atgaggattt ggaagagtca ccctttattt agtctggtta atggttatct tatcgattca      60
ccacaaccaa gtaatctaag ctatctatga aatttcggtt cattactggg attttgtctt     120
gtaatacaaa tcgttactgg tgttacactt gctatgcatt ataaccctag cgtatctgaa     180
gcatttaact cagttgaaca cataatgaga gatgtaaac                            219
```

<210> SEQ ID NO 8
<211> LENGTH: 172
<212> TYPE: DNA
<213> ORGANISM: Zymoseptoria tritici

<400> SEQUENCE: 8

```
tatctgaagc atttaactca gttgaacaca taatgagaga tgtaaacaat ggatgactta      60
tacgttatct tcactctaat actgcttcag ctttcttctt tttagtttac ctgcacgtgg     120
gtagagggtt atactacggg tcatacaaag ccccctagaac attaacatga ac            172
```

<210> SEQ ID NO 9
<211> LENGTH: 258
<212> TYPE: DNA
<213> ORGANISM: Zymoseptoria tritici

<400> SEQUENCE: 9

```
gttatggcta accctatgca aactccacct gctatagtgc ctgaatgata tttattacct      60
ttctacgcta tactaagatc aatacctaac aaactattag gtgtgatcgc aatgttttct     120
gctatattga ttataatgat aatgccaatt accgatttag gtagaagtag aggattacag     180
tttagaccct taagcaagat cacatttac atatttgttg ctaacttctt agtattaatg     240
caattaggtg ctaatcac                                                   258
```

<210> SEQ ID NO 10
<211> LENGTH: 221
<212> TYPE: DNA
<213> ORGANISM: Zymoseptoria tritici

<400> SEQUENCE: 10

```
gattacagtt tagacccttta agcaagatca cattttacat atttgttgct aacttcttag     60
tattaatgca attaggtgct aatcacgttg agtcaccatt tatagaattt gggcaaatta    120
gtacagtact gtacttttca catttcttaa tcatagtgcc tctagtaagc ttaatcgaga    180
atactttagt ggatatgcac ttaaacaaca caataacgta a                        221
```

<210> SEQ ID NO 11

```
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 11
gttctgatga tggcaaccgc                                                       20

<210> SEQ ID NO 12
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 12
aggatttcct gaacccgctg                                                       20

<210> SEQ ID NO 13
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 13
acacgataca gcgggttcag                                                       20

<210> SEQ ID NO 14
<211> LENGTH: 21
<212> TYPE: DNA
<213> ORGANISM: Artificial Sequence
<220> FEATURE:
<223> OTHER INFORMATION: synthesized primer oligonucleotide

<400> SEQUENCE: 14
caggtggagt ttgcataggg t                                                     21

<210> SEQ ID NO 15
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 15
ttacctgcac gtgggtagag                                                       20

<210> SEQ ID NO 16
<211> LENGTH: 20
<212> TYPE: DNA
<213> ORGANISM: Artificial Sequence
<220> FEATURE:
<223> OTHER INFORMATION: synthesized primer oligonucleotide

<400> SEQUENCE: 16
accctaagaa tgcggttgcc                                                       20

<210> SEQ ID NO 17
<211> LENGTH: 996
<212> TYPE: DNA
<213> ORGANISM: Puccinia triticina

<400> SEQUENCE: 17

```
ccacaaccag caaatattag ttatatatgg aactttggga gtcttctagg atgttgtcta    120
atcattcaga taattacagg ggtaactcta gcgatgcatt atacacctag tgtagatctg    180
gcatttattt cagtagagca tatcataagg gatgtagaat atggttgact gattaggtat    240
cttcacgcta atgtagcctc ttttttttc attttgtat atctacacgt tggaagaggg      300
ctatactacg gttcttacaa gtcaccaagg acacttctat gagccattgg tgtaattatt    360
ctaattgtaa taatagcgac tgcctttatg ggttacgttc taccttacgg acagatgtca    420
ctatgaggtg caacagtaat tacgaatcta ataagtgcga ttccatgagt gggtggggat    480
ctagtagaat ttatttgagg aggggtttagt gtaaacaatg cgactctgaa cagattttt    540 agtcttcatt ttgtactacc tttcattcta gctgcactag tagtaataca tcttctcacg    600
ctacatgagc acggttcaaa taatcctcta ggggtgacag ggaatgcgga taggctgcca    660
atggctccta atttatttt caaagaccta gtaaccattt tccttttcct tctagttcta     720
gctattttcg ttatgtatgc acctaacata taggggcatt cagataatta tatcccagct   780
aatccgatac agacaccagc ttcgattgta cctgagtggt atcttcttcc attctatgct    840
attctacgtt caattcctaa taagctacta ggggtgatag ccatgtttgc aagtcttcta    900
atcctgctag ccataccggt aatagaccgg agcagaatga gagggagtca atttagacct    960
cttaatagat ttatttctg agttctggct cgaaac                                996

<210> SEQ ID NO 18
<211> LENGTH: 1161
<212> TYPE: DNA
<213> ORGANISM: Cercospora beticola

<400> SEQUENCE: 18
atgagaatat ttaaaagtca ccctttatta agtttagtta atggttattt agttgattca     60
cctcagcctt caaatattag ttacctgtga aactttggtt cactattagg attttgtctt    120
gtaatacaaa tcgtaacagg agttacttta gctatgcact acaatcctag cgtacttgaa    180
gcatttaatt cagtagaaca tattatgaga gacgtaaata acggatgatt aatacgttac    240
ttacactcta atacagcttc agcatttttc ttcttagtat atttacacgt aggaagaggt    300
ctatactatg gttcttacaa agcacctaga acattggtat gaactatagg tactattata    360
ttagttttaa tgatggctac agccttcttg ggttatgttt taccttacgg acaaatgtct    420
ttatgaggtg caactgttat tactaattta atgagtgcaa taccatgagt aggacaagac    480
atagttgagt tttatgagg aggttttct gttaataacg caacattaaa tagatttttt      540
gcattgcatt ttgtattacc tttcgtatta gctgcattag ctttaatgca cttaattgct    600
ttacatgata gtgcaggttc aggtaatcct ttaggagttt ctggtaatta tgacagactt    660
ccttttgctc catactttat atttaaagat ttaataacta tattcttatt tataatagtg    720
ctatcagtgt ttgttttctt catgccgaac gtttttaggtg atagtgagaa ttacgttgtg    780
gccaatccaa tgcaaacacc tcctgctata gtaccagaat gatatttatt acctttctat    840
gctatattaa gatctatacc taacaaacta ttaggtgtta ttgctatgtt ttctgccata    900
ttaataatac taactatgcc tttcacagac ctaggtagaa gtagaggatt acagttcaga    960
cctttaagta aaatagcatt ttacattttt gtagcaaatt tcttattatt gatgcaattg   1020
ggtgctaaac acgttgaatc accattcata gaatttggtc aaataagtac tgttttatat   1080
ttttcacatt tcttgataat agttccttta gttagtttat tagaaaatag tttaattgaa   1140
```
ttacatttaa ataaaaaata a                                           1161

<210> SEQ ID NO 19
<211> LENGTH: 1182
<212> TYPE: DNA
<213> ORGANISM: Magnaporthe grisea

<400> SEQUENCE: 19
atgagaatat taaaaagtca ttcattatta aaattagtga attcttacct tatcgatgcg    60
tcacaaccaa gtaacattag ttacttgtga aattttggtt cattattagc tgtttgttta   120
atagtacaaa ttattaccgg tattacatta gctatgcatt atagtcctag tgtaatggaa   180
gcttttaact caatagagca tataatgaga gatgttaata acgggtgatt agttcgttat   240
ctacatagta atacagcttc tgctttcttt ttcttagtgt atttacacat aggaagaggt   300
atatattacg gatcatatag agctcctcgt actttagttt gagctattgg tactgttata   360
ttaatattaa tgatggctat cggtttccta ggttatgttt taccttatgg acagatgtca   420
ttatgaggtg ctacagttat tactaatctt attagtgcta taccttgaat agggcaagat   480
attgttgaat tcatttgagg tggttttttct gttaataatg ccactttaaa cagatttttt   540
gcattacatt ttgtattgcc ttttgtatta gctgctttag ttttaatgca cttaattgca   600
cttcatgata ctgctggttc aagcaatcct cttggtgttt caggtaatta cgatagaatt   660
acatttgctc catattttt atttaaagat ttaattacta tttttatatt tatttttgta   720
ttaagtgctt ttgtattctt tatgcctaat gttttagggg atagtgataa ttatattatg   780
gctaatccta tgcaaactcc tgctgctatt gtacctgaat gatacttatt accttttctat   840
gctattttaa gatctatacc taataaatta ttaggtgtta tagcgatgtt tagtgctatt   900
ttagctatta tgttattacc tgttacagat ttaggtagat ctagaggttt acaatttaga   960
ccatttagta aaatagcttt ctgagttttt gttgctaatt tcttagtttt aatgcaatta  1020
ggtgctaaac acgttgaaga tccatttata ttattaggtc aattaagtac tgtattatac  1080
tttagttatt ttgttgctat attacctttta gctagttact tagataatag tttaactgat  1140
ttatctaata aatctgaatt attttttaaat aaaactaact aa                     1182

<210> SEQ ID NO 20
<211> LENGTH: 1227
<212> TYPE: DNA
<213> ORGANISM: Phaeosphaeria nodorum

<400> SEQUENCE: 20
atgagattat taaaaagcca tcctatttta aggttagcga attcttactt agtagattca    60
ccacaacctt taaatttaag ttatatgtga aattttggtt ctttattagg tgtttgttta   120
attatacaaa ttgttacagg tgtaacatta gcgatgcatt ataaccctag tgtagcagaa   180
gcatttaata gtgttgagca tattatgcgt gatgtaaata atggatgatt agtacgttac   240
ttacacagta atactgcttc agcatttttc ttcatagttt acttacacat aggtagaggt   300
ttatactacg gatcatatag agcaccaaga actctagtat gaactattgg tactgttata   360
tttattttaa tgatggctac agcttttcttg ggatacgtcc ttccttatgg gcaaatgtca   420
ctatgaggtg caacagttat tactaaccttt atgagtgcta ttccttgagt aggacaagat   480
attgttgaat ttatttgagg tgtttgtttc aaatgaagtt accaacacaa atgctctgtt   540
aacaatgcta cattaaatag attcttctca ttacacttcg ttttacctttt tgtcttagct   600
gctttagtac taatgcattt aatcgtttta catgacacat cggggtcagg aaatccttta   660

```
ggtatatcag gaaactacga aagaatacct tttgcacctt atttcatatt taaagatctt    720
attacaattt ttgcatttat atttgtatta tctttatttg tgttctttat gccaaacgtt    780
ctgggtgact cagaaaatta tgtagtggcg aatcctatgc aaactcctgc agctattgtt    840
ccagagtgat atcttcttcc tttctacgcc atattaagat ctattcctaa caaattatta    900
ggagtgatag ccatgttctc tgctatcctt atattactgt tactacctat tacagatgta    960
agtagatcaa gaggtatgca atttagacct ttaagtaaat gagctttctt tgtgtttgtg   1020
gctaatttct taatcttaat gcaattagga gctaaacacg tagaatctcc atttattgaa   1080
tttggtcaaa taagtaccgt tttatacttt ttatacttta cagttgtaat gtatggtgtt   1140
acttttattg aaaatacttt tgtggactta aatttctaca ctaatacaaa acattcttcc   1200
cggtttaact ttgttactaa aaaataa                                       1227
```

<210> SEQ ID NO 21
<211> LENGTH: 1191
<212> TYPE: DNA
<213> ORGANISM: Rhynchosporium secalis

<400> SEQUENCE: 21

```
atgagaatat ttaagagtca tcctttatta aaattggtta attcctatat aatcgattca     60
ccacaaccat ctaatctaag ctacttatga aattttggtt ctttattagc cgtttgttta    120
gctatacaaa tagttacagg tgtaacattg gctatgcatt acaaccctag tatattagaa    180
gcgtttaatt ccatagaaca tattatgcgt gatgtaaata acggatgatt aatacgttac    240
ttacatagta acactgcatc tttttcttc ttcctagtgt atttacacat gggtagaggt    300
ttatattatg ggtcatacag agcacctaga acattagtat gaacaatagg tacatttata    360
ttcatattaa tgatcgttac agcattcttg ggttatgtgc ttccttatgg acagatgtct    420
ttatgaggtg ccacagttat aactaatctt atgagtgcta taccttgaat aggtcaagac    480
attgttgagt ttatctgagg gggtttttct gttaataatg caactttaaa tagattcttt    540
gcattacatt ttgttttacc gtttatatta gctgcattag tattaatgca cttaatagcc    600
ttacacgata gtgcagggtc aggtaatcct ttaggtgtat caggtaatta cgatagatta    660
ccttttgctc cttacttctt attcaaagat ttaataacta tctttttatt tatctttgta    720
ttaagtttat tcgtattctt catgcctaac gtattaggtg atagtgaaaa ttacgttgta    780
gctaacccta tgcaaactcc acctgcgata gttccggagt gatatttact acctttctat    840
gctatattaa gatctatacc taacaaatta ttaggtgtta tagctatgct tagtgctata    900
ttagttatat tagctatgcc atttacagat ttaagtagat ctagaggtat acaatttaga    960
cctttaagta aaatagcttt ttatattttt gttgctaatt tcttaatatt aatggtgtta   1020
ggtgctaaac acgttgaatc accattcata gaatttggac aaataagtac cgtaatatat   1080
ttctcacact tttaatcat agtgcctttg gtttctttaa tagaaaacag tttaatagat   1140
ttaaacacgt caatagacta ttcttcgcct tccgttttag aaaaagcgta a            1191
```

<210> SEQ ID NO 22
<211> LENGTH: 1188
<212> TYPE: DNA
<213> ORGANISM: Phakopsora pachyrhizi

<400> SEQUENCE: 22

```
atgagaaatt tcaagacgca tccaattcta ggtctagtaa attcgtacat aggggattca     60
```

```
ccgcagccat cgaacatcag ttacatatga aattttggga gtctactagg atgttgtcta    120
atcattcaga ttatcacggg tgtaacacta gcgatgcatt ataccgag tgtggatata      180
gcttttattt cagtagagca tattataagg gatgtagagt acgggtgact aattaggtat    240
ctacatgcga atgtagcatc attttttttt attttgtat atctacatat aggaaggggt     300
ctatactacg gttcgtacaa gtcaccaagg acactagtat gggcgattgg agtaattatt   360
cttattgtaa taatagcgac agcgtttata ggttatgtac taccgtatgg acagatatca   420
ctatgaggtg caacagtaat tacgaatctg ataagtgcga ttccctgaat tggagggat     480
ctagtagaat ttatttgggg gggtttcagt gtaagtaatg cgactctgaa tagatttttt   540
agtattcatt ttgtactacc gttcattata gcggcactag cggcgataca tctactaact   600
ctacatgagc atggttcaag taatccactg ggtgtaacag ggaatgcgga ccggctaccg   660
atagcaccat atttattt caaggatcta gtaactattt ttatattctt tctagttcta     720
gcaatatttg taatgtatgc accgaatcta ataggtcatt cagacaatta tattccagcg   780
aatccaatac agacaccggc atcaattgta cctgaatggt atctactacc tttttatgcg   840
attctacgat cgattccgaa caagctacta ggtgtaatag cgatatttgc gagtctacta   900
attctactag cgataccgt aatggatatg agtagggtaa gagggagtca atttaggcca    960
ctaaataggt ttatttttg agtactggta tcagatttg tagtactaat gtatctagga    1020
tctcagcatg tggagcagcc atatattata gtaggtcagg tagcaacagg actatacttt  1080
gcttgatttg tagtgctagt accagtaacc tcgatcattg agaatactct gatagatctt  1140
aatgatgtgg gtatagagag tagtaagaac ataatatgat cagcttag                1188
```

<210> SEQ ID NO 23
<211> LENGTH: 1266
<212> TYPE: DNA
<213> ORGANISM: Venturia inaequalis

<400> SEQUENCE: 23

```
agcttatata aaaaaatctc acttttcaa tttgatatgc gaattttaaa aagtcatcca    60
ctattgagat tagccaattc ttatataatt gattccccac aaccctctaa cataagttac   120
ctgtgaaatt tcggttcttt attagcattc tgtttagtta tacaaattat aactggtgtt   180
actttagcaa tgcactacaa tcctagtgtg ctagaagcat ttaattccgt tgagcatatt   240
atgcgagacg ttaacaatgg atgattaata cgatatttac acgctaatac tgcttcagct   300
ttcttcttca tagtctattt gcatatggga agagggctat attacggttc ttatagagca   360
cctagaacgt tagtatgaac tttaggtgta attatcttta tattaatgat agttacagcc   420
ttcctgggtt atgttttacc ttatggtcaa atgagcctat ggggtgcaac tgtcatcaca   480
aaccttatga gtgctatacc gtgaatagga caagatatag tcgaatttct gtggggaggc   540
ttttcagtga acaacgctac tttaaacaga ttttttgcac tacattttgt actacctttc   600
gtattagcag cactagcttt aatgcactta attgcattac atgacagtgc gggatcgggt   660
aaccctttag gtgtgtcagg taactttgac agactaccct tgctccctta tttcatattt  720
aaagatttaa taactatctt ttattttata ttaggattat ctatctttgt tttcttcgca   780
cctaatatat taggtgatag tgaaaattac gtggttgcta accctatgca aacaccacct  840
gccatagtac cggagtgata tcttcttcct ttttatgcta tattaagatc tatacctaat   900
aaattgttag gtgttatagc tatgtttgca gctatagtga tcttattagt tatgccattt   960
actgatttag gtagaagtag aggtatacaa tttagaccat taagtaaaat agcttactat  1020
```

```
ttctttatag ctaattttt aattttaatg aaattaggtg ctaaacatgt tgaatctcca    1080
tttattgagt ttggacaaat tagtactgtt ttatactttt ctcactttgt gattattgta    1140
cctcttgtat cattaataga gaatacttta gtggacttac atcttcataa tactttatca    1200
cttaaaaatg ttttttaatg tcggataaaa gggcagataa caatggtaat gggaaatgat    1260
gaatat                                                                1266

<210> SEQ ID NO 24
<211> LENGTH: 589
<212> TYPE: DNA
<213> ORGANISM: Alternaria solani

<400> SEQUENCE: 24
aggtttgtat tgtggttctt acagagcacc tagaactcta gtatgaacta ttggtactgt      60
tatctttatc ttaatgatgg ctacagcttt cctgggttat gttcttcctt atgggcaaat    120
gtctttatga ggtgctacag ttattactaa cctatgagt gctatcctt gagtaggaca      180 agatattgtt gagttcattt gaggaggttt cagtgttaac aatgcaacat aaatagatt     240 cttctcatta catttcgttt tacctttcgt attagctgct ttagcactaa tgcacttaat    300
cgttttacac gatacagctg gatcaggaaa tcctttaggt gtatcaggaa actacgaaag    360
aatatctttt gctccttatt tcatatttaa agatcttatt acaatatttg catttatatt    420
tgtattatct ttatttgtgt tctttatgcc taatgtatta ggagatagtg aaaactatgt    480
tgtggcaaac cctatgcaaa ctcctgcagc tatcgtgcca gaatgatacc ttctgccttt    540
ctatgctata ttaagatcta tacctaacaa attattagga gttatagcg             589

<210> SEQ ID NO 25
<211> LENGTH: 996
<212> TYPE: DNA
<213> ORGANISM: Puccinia striiformis

<400> SEQUENCE: 25
atgagaattc ttaagacgca tccgattcta ggtctagtta attcttatat aggggattca      60
ccacaaccag ccaatattag ttatatatgg aactttggaa gtcttctagg atgttgtctt    120
atcattcaga ttattacagg agtaactcta gcgatgcatt atacaccaag tgttgatcta    180
gcctttattt cagtggagca tatcataaga gatgttgaat atggttgact gattaggtat    240
cttcacgcta atgtagcttc tttttttttc attttgtat atatacacat tggaagaggg    300
ctatactacg gttcttacaa gtcaccaagg acacttctat gagccattgg tgtaattatt    360
ctaattgtta taatagcgac agcctttatg ggatacgttc taccttacgg acagatgtca    420
ctatgaggtg caacagtaat tacgaatcta ataagtgcaa ttccatgagt gggtggggat    480
cttgttgaat ttatttgagg agggtttagt gttaacaatg cgactctgaa cagattttt    540 agtcttcatt ttgtactacc tttcattctt gctgcacttg ttgtaataca tcttctcacg    600
cttcatgagc atggttctaa taatcctctt ggggtttcag ggaatgcgga taggctgcca    660
atggctccta attatatttt caaggaccta gttaccattt tccttttcct tcttgttctt    720
gctatgttcg taatgtatgc accaaacata tagggcatt ctgataatta tatcccagct    780
aatccgatac agacaccagc ttcgatcgta cctgagtgat atcttcttcc attctatgct    840
attctacgtt ctattcctaa taaactacta ggggtgatag ccatggttgc aagtcttcta    900
atcctgcttg ccataccggt aatagaccga atcagaatga gaaggagtca atttagacct    960
```

```
cttaatagat ttaatttctg agatccggct cgaaac                                996
```

<210> SEQ ID NO 26
<211> LENGTH: 1173
<212> TYPE: DNA
<213> ORGANISM: Zymoseptoria tritici

<400> SEQUENCE: 26

```
ttattttacg ttatttgtgt tgtttaagtg catatccact aaagtattct cgattaagct     60
tactagaggc actatgatta agaaatgtga aaagtacagt actgtactaa tttgcccaaa    120
ttctataaat ggtgactcaa cgtgtttagc acctaattgc attaatacta agaagttagc    180
aacaaatatg taaaatgtga tcttgcttaa aggtctaaat tgtaatcctc tacttctacc    240
taaatcggta attggcatta tcattataat caatatagca gaaaacattg cgatcacacc    300
taatagtttg ttaggtattg atcttagtat agcgtagaaa ggtaataaat atcattcagg    360
cactatagca ggtggagttt gcatagggtt agccataaca taattctcgc tgtcacctaa    420
aacgttaggc ataagaaaaa caaatattga taacactata atgaataaaa atattgttat    480
taaatctttg aatataaagt aaggggcgaa tggtaatcta tcgtagttac ctgatacacc    540
taaaggattt cctgaacccg ctgtatcgtg taaagctatt agatgcatta aaactaatgc    600
agctaacaca aacggtaaaa cgaaatgtag agcaaagaat ctgttcaatg ttgcattgtt    660
aacagaaaat ccacctcata cgaattcaac tatgtcttgt ccaactcaag gtattgcact    720
caataagtta gttataactg ttgctcctca taaagacatt tgaccataag gtaatacata    780
ccctaagaat gcggttgcca tcatcagaac tagtattata gtaccgattg ttcatgttaa    840
tgttctaggg gctttgtatg acccgtagta taaccctcta cccacgtgca ggtaaactaa    900
aaagaagaaa gctgaagcag tattagagtg aagataacgt ataagtcatc cattgtttac    960
atctctcatt atgtgttcaa ctgagttaaa tgcttcagat acgctagggt tataatgcat   1020
agcaagtgta acaccagtaa cgatttgtat tacaagacaa atcccagta atgaaccgaa    1080
atttcataga tagcttagat tacttggttg tggtgaatcg ataagataac cattaaccag   1140
actaaataaa gggtgactct ttcaaatcct cat                                1173
```

<210> SEQ ID NO 27
<211> LENGTH: 1173
<212> TYPE: DNA
<213> ORGANISM: Zymoseptoria tritici

<400> SEQUENCE: 27

```
ttattttacg ttatttgtgt tgtttaagtg catatccact aaagtattct cgattaagct     60
tactagaggc actatgatta agaaatgtga aaagtacagt actgtactaa tttgcccaaa    120
ttctataaat ggtgactcaa cgtgtttagc acctaattgc attaatacta agaagttagc    180
aacaaatatg taaaatgtga tcttgcttaa aggtctaaat tgtaatcctc tacttctacc    240
taaatcggta attggcatta tcattataat caatatagca gaaaacattg cgatcacacc    300
taatagtttg ttaggtattg atcttagtat agcgtagaaa ggtaataaat atcattcagg    360
cactatagca ggtggagttt gcatagggtt agccataaca taattctcgc tgtcacctaa    420
aacgttaggc ataagaaaaa caaatattga taacactata atgaataaaa atattgttat    480
taaatctttg aatataaagt aaggggcgaa tggtaatcta tcgtagttac ctgatacacc    540
taaaggattt cctgaacccg ctgtatcgtg taaagctatt agatgcatta aaactaatgc    600
agctaacaca aacggtaaaa cgaaatgtag agcaaagaat ctgttcaatg ttgcattgtt    660
```

| | | |
|---|---|---|
| aacagaaaat ccacctcata cgaattcaac tatgtcttgt ccaactcaag gtattgcact | 720 | |
| caataagtta gttataactg ttgctgctca taaagacatt tgaccataag gtaatacata | 780 | |
| ccctaagaat gcggttgcca tcatcagaac tagtattata gtaccgattg ttcatgttaa | 840 | |
| tgttctaggg gctttgtatg acccgtagta taaccctcta cccacgtgca ggtaaactaa | 900 | |
| aaagaagaaa gctgaagcag tattagagtg aagataacgt ataagtcatc cattgtttac | 960 | |
| atctctcatt atgtgttcaa ctgagttaaa tgcttcagat acgctagggt tataatgcat | 1020 | |
| agcaagtgta acaccagtaa cgatttgtat tacaagacaa aatcccagta atgaaccgaa | 1080 | |
| atttcataga tagcttagat tacttggttg tggtgaatcg ataagataac cattaaccag | 1140 | |
| actaaataaa gggtgactct ttcaaatcct cat | 1173 | |

<210> SEQ ID NO 28
<211> LENGTH: 1173
<212> TYPE: DNA
<213> ORGANISM: Zymoseptoria tritici

<400> SEQUENCE: 28

| | | |
|---|---|---|
| ttattttacg ttatttgtgt tgtttaagtg catatccact aaagtattct cgattaagct | 60 | |
| tactagaggc actatgatta agaaatgtga aaagtacagt actgtactaa tttgcccaaa | 120 | |
| ttctataaat ggtgactcaa cgtgtttagc acctaattgc attaatacta agaagttagc | 180 | |
| aacaaatatg taaaatgtga tcttgcttaa aggtctaaat tgtaatcctc tacttctacc | 240 | |
| taaatcggta attggcatta tcattataat caatatagca gaaaacattg cgatcacacc | 300 | |
| taatagtttg ttaggtattg atcttagtat agcgtagaaa ggtaataaat atcattcagg | 360 | |
| cactatagca ggtggagttt gcatagggtt agccataaca taattctcgc tgtcacctaa | 420 | |
| aacgttaggc ataagaaaaa caaatattga taacactata atgaataaaa atattgttat | 480 | |
| taaatctttg aatataaagt aaggggcgaa tggtaatcta tcgtagttac ctgatacacc | 540 | |
| taaaggattt cctgaacccg ctgtatcgtg taaagctatt agatgcatta aaactaatgc | 600 | |
| agctaacaca aacggtaaaa cgaaatgtag agcaaagaat ctgttcaatg ttgcattgtt | 660 | |
| aacagaaaat ccacctcata cgaattcaac tatgtcttgt ccaactcaag gtattgcact | 720 | |
| caataagtta gttataactg ttgctgctca taaagacatt tgaccataag gtaatacata | 780 | |
| ccctaagaat gcggttgcca tcatcagaac tagtattata gtaccgattg ttcatgttaa | 840 | |
| tgttctaggg gctttgtatg acccgtagta taaccctcta cccacgtgca ggtaaactaa | 900 | |
| aaagaagaaa gctgaagcag tattagagtg aagataacgt ataagtcatc cattgtttac | 960 | |
| atctctcatt atgtgttcaa ctgagttaaa tgcttcagat acgctagggt tataatgcat | 1020 | |
| agcaagtgta acaccagtaa cgatttgtat tacaagacaa aatcccagta atgaaccgaa | 1080 | |
| atttcataga tagcttagat tacttggttg tggtgaatcg ataagataac cattaaccag | 1140 | |
| actaaataaa gggtgactct ttcaaatcct cat | 1173 | |

<210> SEQ ID NO 29
<211> LENGTH: 1173
<212> TYPE: DNA
<213> ORGANISM: Zymoseptoria tritici

<400> SEQUENCE: 29

| | | |
|---|---|---|
| ttattttacg ttatttgtgt tgtttaagtg catatccact aaagtattct cgattaagct | 60 | |
| tactagaggc actatgatta agaaatgtga aaagtacagt actgtactaa tttgcccaaa | 120 | |

```
ttctataaat ggtgactcaa cgtgtttagc acctaattgc attaatacta agaagttagc    180
aacaaatatg taaaatgtga tcttgcttaa aggtctaaat tgtaatcctc tacttctacc    240
taaatcggta attggcatta tcattataat caatatagca gaaaacattg cgatcacacc    300
taatagtttg ttaggtattg atcttagtat agcgtagaaa ggtaataaat atcattcagg    360
cactatagca ggtggagttt gcatagggtt agccataaca taattctcgc tgtcacctaa    420
aacgttaggc ataagaaaaa caaatattga taacactata atgaataaaa atattgttat    480
taaatctttg aatataaagt aaggggcgaa tggtaatcta tcgtagttac ctgatacacc    540
taaaggattt cctgaacccg ctgtatcgtg taaagctatt agatgcatta aaactaatgc    600
agctaacaca acggtaaaa cgaaatgtag agcaaagaat ctgttcaatg ttgcattgtt    660
aacagaaaat ccacctcata cgaattcaac tatgtcttgt ccaactcaag gtattgcact    720
caataagtta gttataactg ttgctgctca taaagacatt tgaccataag gtaatacata    780
ccctaagaat gcggttgcca tcatcagaac tagtattata gtaccgattg ttcatgttaa    840
tgttctaggg gctttgtatg acccgtagta taaccctcta cccacgtgca ggtaaactaa    900
aaagaagaaa gctgaagcag tattagagtg aagataacgt ataagtcatc cattgtttac    960
atctctcatt atgtgttcaa ctgagttaaa tgcttcagat acgctagggt tataatgcat   1020
agcaagtgta acaccagtaa cgatttgtat tacaagacaa aatcccagta atgaaccgaa   1080
atttcataga tagcttagat tacttggttg tggtgaatcg ataagataac cattaaccag   1140
actaaataaa gggtgactct ttcaaatcct cat                                1173

<210> SEQ ID NO 30
<211> LENGTH: 1173
<212> TYPE: DNA
<213> ORGANISM: Zymoseptoria tritici

<400> SEQUENCE: 30
ttattttacg ttatttgtgt tgtttaagtg catatccact aaagtattct cgattaagct     60
tactagaggc actatgatta agaaatgtga aaagtacagt actgtactaa tttgcccaaa    120
ttctataaat ggtgactcaa cgtgtttagc acctaattgc attaatacta agaagttagc    180
aacaaatatg taaaatgtga tcttgcttaa aggtctaaat tgtaatcctc tacttctacc    240
taaatcggta attggcatta tcattataat caatatagca gaaaacattg cgatcacacc    300
taatagtttg ttaggtattg atcttagtat agcgtagaaa ggtaataaat atcattcagg    360
cactatagca ggtggagttt gcatagggtt agccataaca taattctcgc tgtcacctaa    420
aacgttaggc ataagaaaaa caaatattga taacactata atgaataaaa atattgttat    480
taaatctttg aatataaagt aaggggcgaa tggtaatcta tcgtagttac ctgatacacc    540
taaaggattt cctgaacccg ctgtatcgtg taaagctatt agatgcatta aaactaatgc    600
agctaacaca acggtaaaa cgaaatgtag agcaaagaat ctgttcaatg ttgcattgtt    660
aacagaaaat ccacctcata cgaattcaac tatgtcttgt ccaactcaag gtattgcact    720
caataagtta gttataactg ttgctgctca taaagacatt tgaccataag gtaatacata    780
ccctaagaat gcggttgcca tcatcagaac tagtattata gtaccgattg ttcatgttaa    840
tgttctaggg gctttgtatg acccgtagta taaccctcta cccacgtgca ggtaaactaa    900
aaagaagaaa gctgaagcag tattagagtg aagataacgt ataagtcatc cattgtttac    960
atctctcatt atgtgttcaa ctgagttaaa tgcttcagat acgctagggt tataatgcat   1020
agcaagtgta acaccagtaa cgatttgtat tacaagacaa aatcccagta atgaaccgaa   1080
```

```
atttcataga tagcttagat tacttggttg tggtgaatcg ataagataac cattaaccag    1140
actaaataaa gggtgactct ttcaaatcct cat                                 1173

<210> SEQ ID NO 31
<211> LENGTH: 1173
<212> TYPE: DNA
<213> ORGANISM: Zymoseptoria tritici

<400> SEQUENCE: 31
ttattttacg ttatttgtgt tgtttaagtg catatccact aaagtattct cgattaagct     60
tactagaggc actatgatta agaaatgtga aaagtacagt actgtactaa tttgcccaaa    120
ttctataaat ggtgactcaa cgtgtttagc acctaattgc attaatacta agaagttagc    180
aacaaatatg taaaatgtga tcttgcttaa aggtctaaat tgtaatcctc tacttctacc    240
taaatcggta attggcatta tcattataat caatatagca gaaaacattg cgatcacacc    300
taatagtttg ttaggtattg atcttagtat agcgtagaaa ggtaataaat atcattcagg    360
cactatagca ggtggagttt gcatagggtt agccataaca taattctcgc tgtcacctaa    420
aacgttaggc ataagaaaaa caaatattga taacactata atgaataaaa atattgttat    480
taaatctttg aatataaagt aaggggcgaa tggtaatcta tcgtagttac ctgatacacc    540
taaaggattt cctgaacccg ctgtatcgtg taaagctatt agatgcatta aaactaatgc    600
agctaacaca aacggtaaaa cgaaatgtag agcaaagaat ctgttcaatg ttgcattgtt    660
aacagaaaat ccacctcata cgaattcaac tatgtcttgt ccaactcaag gtattgcact    720
caataagtta gttataactg ttgctcctca taaagacatt tgaccataag gtaatacata    780
ccctaagaat gcggttgcca tcatcagaac tagtattata gtaccgattg ttcatgttaa    840
tgttctaggg gctttgtatg acccgtagta taaccctcta cccacgtgca ggtaaactaa    900
aaagaagaaa gctgaagcag tattagagtg aagataacgt ataagtcatc cattgtttac    960
atctctcatt atgtgttcaa ctgagttaaa tgcttcagat acgctagggt tataatgcat   1020
agcaagtgta acaccagtaa cgatttgtat tacaagacaa aatcccagta atgaaccgaa   1080
atttcataga tagcttagat tacttggttg tggtgaatcg ataagataac cattaaccag   1140
actaaataaa gggtgactct ttcaaatcct cat                                 1173

<210> SEQ ID NO 32
<211> LENGTH: 1173
<212> TYPE: DNA
<213> ORGANISM: Zymoseptoria tritici

<400> SEQUENCE: 32
ttattttacg ttatttgtgt tgtttaagtg catatccact aaagtattct cgattaagct     60
tactagaggc actatgatta agaaatgtga aaagtacagt actgtactaa tttgcccaaa    120
ttctataaat ggtgactcaa cgtgtttagc acctaattgc attaatacta agaagttagc    180
aacaaatatg taaaatgtga tcttgcttaa aggtctaaat tgtaatcctc tacttctacc    240
taaatcggta attggcatta tcattataat caatatagca gaaaacattg cgatcacacc    300
taatagtttg ttaggtattg atcttagtat agcgtagaaa ggtaataaat atcattcagg    360
cactatagca ggtggagttt gcatagggtt agccataaca taattctcgc tgtcacctaa    420
aacgttaggc ataagaaaaa caaatattga taacactata atgaataaaa atattgttat    480
taaatctttg aatataaagt aaggggcgaa tggtaatcta tcgtagttac ctgatacacc    540
```

```
taaaggattt cctgaacccg ctgtatcgtg taaagctatt agatgcatta aaactaatgc      600
agctaacaca acggtaaaa cgaaatgtag agcaaagaat ctgttcaatg ttgcattgtt      660
aacagaaaat ccacctcata cgaattcaac tatgtcttgt ccaactcaag gtattgcact      720
caataagtta gttataactg ttgctcctca taaagacatt tgaccataag gtaatacata      780
ccctaagaat gcggttgcca tcatcagaac tagtattata gtaccgattg ttcatgttaa      840
tgttctaggg gctttgtatg acccgtagta taaccctcta cccacgtgca ggtaaactaa      900
aaagaagaaa gctgaagcag tattagagtg aagataacgt ataagtcatc cattgtttac      960
atctctcatt atgtgttcaa ctgagttaaa tgcttcagat acgctagggt tataatgcat     1020
agcaagtgta acaccagtaa cgatttgtat tacaagacaa aatcccagta atgaaccgaa     1080
atttcataga tagcttagat tacttggttg tggtgaatcg ataagataac cattaaccag     1140
actaaataaa gggtgactct ttcaaatcct cat                                  1173
```

<210> SEQ ID NO 33
<211> LENGTH: 1173
<212> TYPE: DNA
<213> ORGANISM: Zymoseptoria tritici

<400> SEQUENCE: 33

```
ttattttacg ttatttgtgt tgtttaagtg catatccact aaagtattct cgattaagct       60
tactagaggc actatgatta agaaatgtga aaagtacagt actgtactaa tttgcccaaa      120
ttctataaat ggtgactcaa cgtgtttagc acctaattgc attaatacta agaagttagc      180
aacaaatatg taaaatgtga tcttgcttaa aggtctaaat tgtaatcctc tacttctacc      240
taaatcggta attggcatta tcattataat caatatagca gaaaacattg cgatcacacc      300
taatagtttg ttaggtattg atcttagtat agcgtagaaa ggtaataaat atcattcagg      360
cactatagca ggtggagttt gcataggtt agccataaca taattctcgc tgtcacctaa      420
aacgttaggc ataagaaaa caaatattga taacactata atgaataaaa atattgttat      480
taaatctttg aatataaagt aaggggcgaa tggtaatcta tcgtagttac ctgatacacc      540
taaaggattt cctgaacccg ctgtatcgtg taaagctatt agatgcatta aaactaatgc      600
agctaacaca acggtaaaa cgaaatgtag agcaaagaat ctgttcaatg ttgcattgtt      660
aacagaaaat ccacctcata cgaattcaac tatgtcttgt ccaactcaag gtattgcact      720
caataagtta gttataactg ttgctcctca taaagacatt tgaccataag gtaatacata      780
ccctaagaat gcggttgcca tcatcagaac tagtattata gtaccgattg ttcatgttaa      840
tgttctaggg gctttgtatg acccgtagta taaccctcta cccacgtgca ggtaaactaa      900
aaagaagaaa gctgaagcag tattagagtg aagataacgt ataagtcatc cattgtttac      960
atctctcatt atgtgttcaa ctgagttaaa tgcttcagat acgctagggt tataatgcat     1020
agcaagtgta acaccagtaa cgatttgtat tacaagacaa aatcccagta atgaaccgaa     1080
atttcataga tagcttagat tacttggttg tggtgaatcg ataagataac cattaaccag     1140
actaaataaa gggtgactct ttcaaatcct cat                                  1173
```

<210> SEQ ID NO 34
<211> LENGTH: 1173
<212> TYPE: DNA
<213> ORGANISM: Zymoseptoria tritici

<400> SEQUENCE: 34

```
ttattttacg ttatttgtgt tgtttaagtg catatccact aaagtattct cgattaagct       60
```

```
tactagaggc actatgatta agaaatgtga aaagtacagt actgtactaa tttgcccaaa      120
ttctataaat ggtgactcaa cgtgtttagc acctaattgc attaatacta agaagttagc      180
aacaaatatg taaaatgtga tcttgcttaa aggtctaaat tgtaatcctc tacttctacc      240
taaatcggta attggcatta tcattataat caatatagca gaaaacattg cgatcacacc      300
taatagtttg ttaggtattg atcttagtat agcgtagaaa ggtaataaat atcattcagg      360
cactatagca ggtggagttt gcatagggtt agccataaca taattctcgc tgtcacctaa      420
aacgttaggc ataagaaaaa caaatattga taacactata atgaataaaa atattgttat      480
taaatctttg aatataaagt aaggggcgaa tggtaatcta tcgtagttac ctgatacacc      540
taaaggattt cctgaacccg ctgtatcgtg taaagctatt agatgcatta aaactaatgc      600
agctaacaca aacggtaaaa cgaaatgtag agcaaagaat ctgttcaatg ttgcattgtt      660
aacagaaaat ccacctcata cgaattcaac tatgtcttgt ccaactcaag gtattgcact      720
caataagtta gttataactg ttgctcctca taaagacatt tgaccataag gtaatacata      780
ccctaagaat gcggttgcca tcatcagaac tagtattata gtaccgattg ttcatgttaa      840
tgttctaggg gctttgtatg acccgtagta taaccctcta cccacgtgca ggtaaactaa      900
aaagaagaaa gctgaagcag tattagagtg aagataacgt ataagtcatc cattgtttac      960
atctctcatt atgtgttcaa ctgagttaaa tgcttcagat acgctagggt tataatgcat     1020
agcaagtgta acaccagtaa cgatttgtat tacaagacaa aatcccagta atgaaccgaa     1080
atttcataga tagcttagat tacttggttg tggtgaatcg ataagataac cattaaccag     1140
actaaataaa gggtgactct ttcaaatcct cat                                  1173

<210> SEQ ID NO 35
<211> LENGTH: 1173
<212> TYPE: DNA
<213> ORGANISM: Zymoseptoria tritici

<400> SEQUENCE: 35
ttattttacg ttatttgtgt tgtttaagtg catatccact aaagtattct cgattaagct       60
tactagaggc actatgatta agaaatgtga aaagtacagt actgtactaa tttgcccaaa      120
ttctataaat ggtgactcaa cgtgtttagc acctaattgc attaatacta agaagttagc      180
aacaaatatg taaaatgtga tcttgcttaa aggtctaaat tgtaatcctc tacttctacc      240
taaatcggta attggcatta tcattataat caatatagca gaaaacattg cgatcacacc      300
taatagtttg ttaggtattg atcttagtat agcgtagaaa ggtaataaat atcattcagg      360
cactatagca ggtggagttt gcatagggtt agccataaca taattctcgc tgtcacctaa      420
aacgttaggc ataagaaaaa caaatattga taacactata atgaataaaa atattgttat      480
taaatctttg aatataaagt aaggggcgaa tggtaatcta tcgtagttac ctgatacacc      540
taaaggattt cctgaacccg ctgtatcgtg taaagctatt agatgcatta aaactaatgc      600
agctaacaca aacggtaaaa cgaaatgtag agcaaagaat ctgttcaatg ttgcattgtt      660
aacagaaaat ccacctcata cgaattcaac tatgtcttgt ccaactcaag gtattgcact      720
caataagtta gttataactg ttgctgctca taaagacatt tgaccataag gtaatacata      780
ccctaagaat gcggttgcca tcatcagaac tagtattata gtaccgattg ttcatgttaa      840
tgttctaggg gctttgtatg acccgtagta taaccctcta cccacgtgca ggtaaactaa      900
aaagaagaaa gctgaagcag tattagagtg aagataacgt ataagtcatc cattgtttac      960
```

| | |
|---|---|
| atctctcatt atgtgttcaa ctgagttaaa tgcttcagat acgctagggt tataatgcat | 1020 |
| agcaagtgta acaccagtaa cgatttgtat tacaagacaa atcccagta atgaaccgaa | 1080 |
| atttcataga tagcttagat tacttggttg tggtgaatcg ataagataac cattaaccag | 1140 |
| actaaataaa gggtgactct ttcaaatcct cat | 1173 |

<210> SEQ ID NO 36
<211> LENGTH: 1173
<212> TYPE: DNA
<213> ORGANISM: Zymoseptoria tritici

<400> SEQUENCE: 36

| | |
|---|---|
| ttatttttacg ttatttgtgt tgtttaagtg catatccact aaagtattct cgattaagct | 60 |
| tactagaggc actatgatta agaaatgtga aagtacagt actgtactaa tttgcccaaa | 120 |
| ttctataaat ggtgactcaa cgtgtttagc acctaattgc attaatacta agaagttagc | 180 |
| aacaaatatg taaaatgtga tcttgcttaa aggtctaaat tgtaatcctc tacttctacc | 240 |
| taaatcggta attggcatta tcattataat caatatagca gaaaacattg cgatcacacc | 300 |
| taatagtttg ttaggtattg atcttagtat agcgtagaaa ggtaataaat atcattcagg | 360 |
| cactatagca ggtggagttt gcatagggtt agccataaca taattctcgc tgtcacctaa | 420 |
| aacgttaggc ataagaaaa caaatattga taacactata atgaataaaa atattgttat | 480 |
| taaatctttg aatataaagt aaggggcgaa tggtaatcta tcgtagttac ctgatacacc | 540 |
| taaaggattt cctgaacccg ctgtatcgtg taaagctatt agatgcatta aaactaatgc | 600 |
| agctaacaca aacggtaaaa cgaaatgtag agcaaagaat ctgttcaatg ttgcattgtt | 660 |
| aacagaaaat ccacctcata cgaattcaac tatgtcttgt ccaactcaag gtattgcact | 720 |
| caataagtta gttataactg ttgctgctca taaagacatt tgaccataag gtaatacata | 780 |
| ccctaagaat gcggttgcca tcatcagaac tagtattata gtaccgattg ttcatgttaa | 840 |
| tgttctaggg gctttgtatg acccgtagta taaccctcta cccacgtgca ggtaaactaa | 900 |
| aaagaagaaa gctgaagcag tattagagtg aagataacgt ataagtcatc cattgtttac | 960 |
| atctctcatt atgtgttcaa ctgagttaaa tgcttcagat acgctagggt tataatgcat | 1020 |
| agcaagtgta acaccagtaa cgatttgtat tacaagacaa atcccagta atgaaccgaa | 1080 |
| atttcataga tagcttagat tacttggttg tggtgaatcg ataagataac cattaaccag | 1140 |
| actaaataaa gggtgactct ttcaaatcct cat | 1173 |

<210> SEQ ID NO 37
<211> LENGTH: 1173
<212> TYPE: DNA
<213> ORGANISM: Zymoseptoria tritici

<400> SEQUENCE: 37

| | |
|---|---|
| ttatttttacg ttatttgtgt tgtttaagtg catatccact aaagtattct cgattaagct | 60 |
| tactagaggc actatgatta agaaatgtga aagtacagt actgtactaa tttgcccaaa | 120 |
| ttctataaat ggtgactcaa cgtgtttagc acctaattgc attaatacta agaagttagc | 180 |
| aacaaatatg taaaatgtga tcttgcttaa aggtctaaat tgtaatcctc tacttctacc | 240 |
| taaatcggta attggcatta tcattataat caatatagca gaaaacattg cgatcacacc | 300 |
| taatagtttg ttaggtattg atcttagtat agcgtagaaa ggtaataaat atcattcagg | 360 |
| cactatagca ggtggagttt gcatagggtt agccataaca taattctcgc tgtcacctaa | 420 |
| aacgttaggc ataagaaaa caaatattga taacactata atgaataaaa atattgttat | 480 |

```
taaatctttg aatataaagt aaggggcgaa tggtaatcta tcgtagttac ctgatacacc      540
taaaggattt cctgaacccg ctgtatcgtg taaagctatt agatgcatta aaactaatgc      600
agctaacaca aacggtaaaa cgaaatgtag agcaaagaat ctgttcaatg ttgcattgtt      660
aacagaaaat ccacctcata cgaattcaac tatgtcttgt ccaactcaag gtattgcact      720
caataagtta gttataactg ttgctgctca taaagacatt tgaccataag gtaatacata      780
ccctaagaat gcggttgcca tcatcagaac tagtattata gtaccgattg ttcatgttaa      840
tgttctaggg gctttgtatg acccgtagta taaccctcta cccacgtgca ggtaaactaa      900
aaagaagaaa gctgaagcag tattagagtg aagataacgt ataagtcatc cattgtttac      960
atctctcatt atgtgttcaa ctgagttaaa tgcttcagat acgctagggt tataatgcat     1020
agcaagtgta acaccagtaa cgatttgtat tacaagacaa atcccagta atgaaccgaa      1080 atttcataga tagcttagat tacttggttg tggtgaatcg ataagataac cattaaccag     1140
actaaataaa gggtgactct ttcaaatcct cat                                  1173
```

<210> SEQ ID NO 38
<211> LENGTH: 1173
<212> TYPE: DNA
<213> ORGANISM: Zymoseptoria tritici

<400> SEQUENCE: 38

```
ttattttacg ttatttgtgt tgtttaagtg catatccact aaagtattct cgattaagct       60
tactagaggc actatgatta agaaatgtga aaagtacagt actgtactaa tttgcccaaa      120
ttctataaat ggtgactcaa cgtgtttagc acctaattgc attaatacta agaagttagc      180
aacaaatatg taaatgtgaa tcttgcttaa aggtctaaat tgtaatcctc tacttctacc      240
taaatcggta attggcatta tcattataat caatatagca gaaaacattg cgatcacacc      300
taatagtttg ttaggtattg atcttagtat agcgtagaaa ggtaataaat atcattcagg      360
cactatagca ggtggagttt gcatagggtt agccataaca taattctcgc tgtcacctaa      420
aacgttaggc ataagaaaaa caaatattga taacactata atgaataaaa atattgttat      480
taaatctttg aatataaagt aaggggcgaa tggtaatcta tcgtagttac ctgatacacc      540
taaaggattt cctgaacccg ctgtatcgtg taaagctatt agatgcatta aaactaatgc      600
agctaacaca aacggtaaaa cgaaatgtag agcaaagaat ctgttcaatg ttgcattgtt      660
aacagaaaat ccacctcata cgaattcaac tatgtcttgt ccaactcaag gtattgcact      720
caataagtta gttataactg ttgctgctca taaagacatt tgaccataag gtaatacata      780
ccctaagaat gcggttgcca tcatcagaac tagtattata gtaccgattg ttcatgttaa      840
tgttctaggg gctttgtatg acccgtagta taaccctcta cccacgtgca ggtaaactaa      900
aaagaagaaa gctgaagcag tattagagtg aagataacgt ataagtcatc cattgtttac      960
atctctcatt atgtgttcaa ctgagttaaa tgcttcagat acgctagggt tataatgcat     1020
agcaagtgta acaccagtaa cgatttgtat tacaagacaa atcccagta atgaaccgaa      1080 atttcataga tagcttagat tacttggttg tggtgaatcg ataagataac cattaaccag     1140
actaaataaa gggtgactct ttcaaatcct cat                                  1173
```

<210> SEQ ID NO 39
<211> LENGTH: 1173
<212> TYPE: DNA
<213> ORGANISM: Zymoseptoria tritici

<400> SEQUENCE: 39

```
ttattttacg ttatttgtgt tgtttaagtg catatccact aaagtattct cgattaagct      60
tactagaggc actatgatta agaaatgtga aaagtacagt actgtactaa tttgcccaaa     120
ttctataaat ggtgactcaa cgtgtttagc acctaattgc attaatacta agaagttagc     180
aacaaatatg taaaatgtga tcttgcttaa aggtctaaat tgtaatcctc tacttctacc     240
taaatcggta attggcatta tcattataat caatatagca gaaaacattg cgatcacacc     300
taatagtttg ttaggtattg atcttagtat agcgtagaaa ggtaataaat atcattcagg     360
cactatagca ggtggagttt gcatagggtt agccataaca taattctcgc tgtcacctaa     420
aacgttaggc ataagaaaaa caaatattga taacactata atgaataaaa atattgttat     480
taaatctttg aatataaagt aaggggcgaa tggtaatcta tcgtagttac ctgatacacc     540
taaaggattt cctgaacccg ctgtatcgtg taaagctatt agatgcatta aaactaatgc     600
agctaacaca aacggtaaaa cgaaatgtag agcaaagaat ctgttcaatg ttgcattgtt     660
aacagaaaat ccacctcata cgaattcaac tatgtcttgt ccaactcaag gtattgcact     720
caataagtta gttataactg ttgctgctca taaagacatt tgaccataag gtaatacata     780
ccctaagaat gcggttgcca tcatcagaac tagtattata gtaccgattg ttcatgttaa     840
tgttctaggg gctttgtatg acccgtagta taaccctcta cccacgtgca ggtaaactaa     900
aaagaagaaa gctgaagcag tattagagtg aagataacgt ataagtcatc cattgtttac     960
atctctcatt atgtgttcaa ctgagttaaa tgcttcagat acgctagggt tataatgcat    1020
agcaagtgta acaccagtaa cgatttgtat tacaagacaa atcccagta atgaaccgaa    1080
atttcataga tagcttagat tacttggttg tggtgaatcg ataagataac cattaaccag    1140
actaaataaa gggtgactct ttcaaatcct cat                                 1173
```

<210> SEQ ID NO 40
<211> LENGTH: 1173
<212> TYPE: DNA
<213> ORGANISM: Zymoseptoria tritici

<400> SEQUENCE: 40

```
ttattttacg ttatttgtgt tgtttaagtg catatccact aaagtattct cgattaagct      60
tactagaggc actatgatta agaaatgtga aaagtacagt actgtactaa tttgcccaaa     120
ttctataaat ggtgactcaa cgtgtttagc acctaattgc attaatacta agaagttagc     180
aacaaatatg taaaatgtga tcttgcttaa aggtctaaat tgtaatcctc tacttctacc     240
taaatcggta attggcatta tcattataat caatatagca gaaaacattg cgatcacacc     300
taatagtttg ttaggtattg atcttagtat agcgtagaaa ggtaataaat atcattcagg     360
cactatagca ggtggagttt gcatagggtt agccataaca taattctcgc tgtcacctaa     420
aacgttaggc ataagaaaaa caaatattga taacactata atgaataaaa atattgttat     480
taaatctttg aatataaagt aaggggcgaa tggtaatcta tcgtagttac ctgatacacc     540
taaaggattt cctgaacccg ctgtatcgtg taaagctatt agatgcatta aaactaatgc     600
agctaacaca aacggtaaaa cgaaatgtag agcaaagaat ctgttcaatg ttgcattgtt     660
aacagaaaat ccacctcata cgaattcaac tatgtcttgt ccaactcaag gtattgcact     720
caataagtta gttataactg ttgctgctca taaagacatt tgaccataag gtaatacata     780
ccctaagaat gcggttgcca tcatcagaac tagtattata gtaccgattg ttcatgttaa     840
tgttctaggg gctttgtatg acccgtagta taaccctcta cccacgtgca ggtaaactaa     900
```
aaagaagaaa gctgaagcag tattagagtg aagataacgt ataagtcatc cattgtttac      960
atctctcatt atgtgttcaa ctgagttaaa tgcttcagat acgctagggt tataatgcat     1020
agcaagtgta acaccagtaa cgatttgtat tacaagacaa atcccagta atgaaccgaa      1080 atttcataga tagcttagat tacttggttg tggtgaatcg ataagataac cattaaccag     1140
actaaataaa gggtgactct ttcaaatcct cat                                  1173

<210> SEQ ID NO 41
<211> LENGTH: 1173
<212> TYPE: DNA
<213> ORGANISM: Zymoseptoria tritici

<400> SEQUENCE: 41
ttattttacg ttatttgtgt tgtttaagtg catatccact aaagtattct cgattaagct       60
tactagaggc actatgatta agaaatgtga aaagtacagt actgtactaa tttgcccaaa      120
ttctataaat ggtgactcaa cgtgtttagc acctaattgc attaatacta agaagttagc      180
aacaaatatg taaaatgtga tcttgcttaa aggtctaaat tgtaatcctc tacttctacc      240
taaatcggta attggcatta tcattataat caatatagca gaaaacattg cgatcacacc      300
taatagtttg ttaggtattg atcttagtat agcgtagaaa ggtaataaat atcattcagg     360
cactatagca ggtggagttt gcataggggtt agccataaca taattctcgc tgtcacctaa    420
aacgttaggc ataagaaaa caaatattga taacactata atgaataaaa atattgttat      480
taaatctttg aatataaagt aaggggcgaa tggtaatcta tcgtagttac ctgatacacc     540
taaaggattt cctgaacccg ctgtatcgtg taaagctatt agatgcatta aaactaatgc     600
agctaacaca aacggtaaaa cgaaatgtag agcaaagaat ctgttcaatg ttgcattgtt     660
aacagaaaat ccacctcata cgaattcaac tatgtcttgt ccaactcaag gtattgcact    720
caataagtta gttataactg ttgctcctca taaagacatt tgaccataag gtaatacata     780
ccctaagaat gcggttgcca tcatcagaac tagtattata gtaccgattg ttcatgttaa    840
tgttctaggg gctttgtatg acccgtagta taaccctcta cccacgtgca ggtaaactaa    900
aaagaagaaa gctgaagcag tattagagtg aagataacgt ataagtcatc cattgtttac      960
atctctcatt atgtgttcaa ctgagttaaa tgcttcagat acgctagggt tataatgcat     1020
agcaagtgta acaccagtaa cgatttgtat tacaagacaa atcccagta atgaaccgaa      1080 atttcataga tagcttagat tacttggttg tggtgaatcg ataagataac cattaaccag     1140
actaaataaa gggtgactct ttcaaatcct cat                                  1173

<210> SEQ ID NO 42
<211> LENGTH: 1173
<212> TYPE: DNA
<213> ORGANISM: Zymoseptoria tritici

<400> SEQUENCE: 42
ttattttacg ttatttgtgt tgtttaagtg catatccact aaagtattct cgattaagct       60
tactagaggc actatgatta agaaatgtga aaagtacagt actgtactaa tttgcccaaa      120
ttctataaat ggtgactcaa cgtgtttagc acctaattgc attaatacta agaagttagc      180
aacaaatatg taaaatgtga tcttgcttaa aggtctaaat tgtaatcctc tacttctacc      240
taaatcggta attggcatta tcattataat caatatagca gaaaacattg cgatcacacc      300
taatagtttg ttaggtattg atcttagtat agcgtagaaa ggtaataaat atcattcagg     360

```
cactatagca ggtggagttt gcatagggtt agccataaca taattctcgc tgtcacctaa    420
aacgttaggc ataaagaaaa caaatattga taacactata atgaataaaa atattgttat    480
taaatctttg aatataaagt aaggggcgaa tggtaatcta tcgtagttac ctgatacacc    540
taaaggattt cctgaacccg ctgtatcgtg taaagctatt agatgcatta aaactaatgc    600
agctaacaca aacggtaaaa cgaaatgtag agcaaagaat ctgttcaatg ttgcattgtt    660
aacagaaaat ccacctcata cgaattcaac tatgtcttgt ccaactcaag gtattgcact    720
caataagtta gttataactg ttgctgctca taaagacatt tgaccataag gtaatacata    780
ccctaagaat gcggttgcca tcatcagaac tagtattata gtaccgattg ttcatgttaa    840
tgttctaggg gctttgtatg acccgtagta taaccctcta cccacgtgca ggtaaactaa    900
aaagaagaaa gctgaagcag tattagagtg aagataacgt ataagtcatc cattgtttac    960
atctctcatt atgtgttcaa ctgagttaaa tgcttcagat acgctagggt tataatgcat   1020
agcaagtgta acaccagtaa cgatttgtat tacaagacaa aatcccagta atgaaccgaa   1080
atttcataga tagcttagat tacttggttg tggtgaatcg ataagataac cattaaccag   1140
actaaataaa gggtgactct ttcaaatcct cat                                1173
```

<210> SEQ ID NO 43
<211> LENGTH: 1173
<212> TYPE: DNA
<213> ORGANISM: Zymoseptoria tritici

<400> SEQUENCE: 43

```
ttattttacg ttatttgtgt tgtttaagtg catatccact aaagtattct cgattaagct     60
tactagaggc actatgatta agaaatgtga aaagtacagt actgtactaa tttgcccaaa    120
ttctataaat ggtgactcaa cgtgtttagc acctaattgc attaatacta agaagttagc    180
aacaaatatg taaaatgtga tcttgcttaa aggtctaaat tgtaatcctc tacttctacc    240
taaatcggta attggcatta tcattataat caatatagca gaaaacattg cgatcacacc    300
taatagtttg ttaggtattg atcttagtat agcgtagaaa ggtaataaat atcattcagg    360
cactatagca ggtggagttt gcatagggtt agccataaca taattctcgc tgtcacctaa    420
aacgttaggc ataaagaaaa caaatattga taacactata atgaataaaa atattgttat    480
taaatctttg aatataaagt aaggggcgaa tggtaatcta tcgtagttac ctgatacacc    540
taaaggattt cctgaacccg ctgtatcgtg taaagctatt agatgcatta aaactaatgc    600
agctaacaca aacggtaaaa cgaaatgtag agcaaagaat ctgttcaatg ttgcattgtt    660
aacagaaaat ccacctcata cgaattcaac tatgtcttgt ccaactcaag gtattgcact    720
caataagtta gttataactg ttgctcctca taaagacatt tgaccataag gtaatacata    780
ccctaagaat gcggttgcca tcatcagaac tagtattata gtaccgattg ttcatgttaa    840
tgttctaggg gctttgtatg acccgtagta taaccctcta cccacgtgca ggtaaactaa    900
aaagaagaaa gctgaagcag tattagagtg aagataacgt ataagtcatc cattgtttac    960
atctctcatt atgtgttcaa ctgagttaaa tgcttcagat acgctagggt tataatgcat   1020
agcaagtgta acaccagtaa cgatttgtat tacaagacaa aatcccagta atgaaccgaa   1080
atttcataga tagcttagat tacttggttg tggtgaatcg ataagataac cattaaccag   1140
actaaataaa gggtgactct ttcaaatcct cat                                1173
```

<210> SEQ ID NO 44
<211> LENGTH: 24

```
<212> TYPE: DNA
<213> ORGANISM: Artificial Sequence
<220> FEATURE:
<223> OTHER INFORMATION: synthesized promotor oligonucleotide

<400> SEQUENCE: 44
ttaatacgac tcactatagg gaga                                          24

<210> SEQ ID NO 45
<211> LENGTH: 250
<212> TYPE: DNA
<213> ORGANISM: Artificial Sequence
<220> FEATURE:
<223> OTHER INFORMATION: synthesized partial coding region

<400> SEQUENCE: 45
tgtagaaatc cttcagctcg gggccgtact tggcgaagca ctgggcgccg taggtcaggg    60
tggtcaccag ggtgctccag ggcacgggca catcgccggt ggtgcagatg aactgggcat   120
ccaccttgcc cacgctggca tcgccgtagc ccttgccgcg gatgctgaag gtgtggccat   180
ccacattgcc ctccatctcc accacgtagg ggatcttgcc gtggaacagc agggcgccgc   240
tggagcccat                                                         250

<210> SEQ ID NO 46
<211> LENGTH: 20
<212> TYPE: DNA
<213> ORGANISM: artificial sequence
<220> FEATURE:
<223> OTHER INFORMATION: Oligonucleotide primer of NIa-1F

<400> SEQUENCE: 46
ctggaccgat cggattaaga                                               20

<210> SEQ ID NO 47
<211> LENGTH: 20
<212> TYPE: DNA
<213> ORGANISM: artificial sequence
<220> FEATURE:
<223> OTHER INFORMATION: Oligonucleotide primer of NIa-3R

<400> SEQUENCE: 47
ctgagaactt ccatggcaca                                               20
```